United States Patent
Wolf et al.

(10) Patent No.: US 11,759,222 B2
(45) Date of Patent: *Sep. 19, 2023

(54) METHODS AND DEVICES TO TREAT NASAL AIRWAYS

(71) Applicant: AERIN MEDICAL INC., Sunnyvale, CA (US)

(72) Inventors: Scott J. Wolf, Menlo Park, CA (US); Andrew Frazier, Sunnyvale, CA (US)

(73) Assignee: Aerin Medical Inc., Sunnyvale, CA (US)

(*) Notice: Subject to any disclaimer, the term of this patent is extended or adjusted under 35 U.S.C. 154(b) by 663 days.

This patent is subject to a terminal disclaimer.

(21) Appl. No.: 16/928,718

(22) Filed: Jul. 14, 2020

(65) Prior Publication Data

US 2020/0375648 A1    Dec. 3, 2020

Related U.S. Application Data

(63) Continuation of application No. 16/041,101, filed on Jul. 20, 2018, now Pat. No. 10,722,282, which is a
(Continued)

(51) Int. Cl.
*A61B 18/12* (2006.01)
*A61B 17/24* (2006.01)
(Continued)

(52) U.S. Cl.
CPC ............... *A61B 17/24* (2013.01); *A61B 5/01* (2013.01); *A61B 17/2816* (2013.01);
(Continued)

(58) Field of Classification Search
CPC ..... A61B 17/24; A61B 18/1206; A61B 18/14; A61B 18/1445; A61B 2018/00577; A61B 2018/126; A61B 2018/0022
See application file for complete search history.

(56) References Cited

U.S. PATENT DOCUMENTS

| | | |
|---|---|---|
| 4,887,605 A | 12/1989 | Angelsen et al. |
| 5,348,008 A | 9/1994 | Bornn et al. |

(Continued)

FOREIGN PATENT DOCUMENTS

| | | |
|---|---|---|
| CN | 101325919 A | 12/2008 |
| WO | 1999007299 | 2/1999 |

(Continued)

OTHER PUBLICATIONS

Buckley et al., "High-resolution spatial mapping of shear properties in cartilage," J Biomech., Mar. 3, 2010;43(4):796-800, Epub Nov. 5, 2009.

(Continued)

*Primary Examiner* — Daniel W Fowler
(74) *Attorney, Agent, or Firm* — Merchant & Gould P.C.

(57) ABSTRACT

A method for reshaping a nasal airway in a patient involves advancing an inflatable balloon of a reshaping device in an uninflated configuration into a nostril of the patient and between a nasal septum and a lateral wall of the nasal airway. The method then involves inflating the inflatable balloon to an inflated configuration to cause the inflatable balloon to contact nasal mucosa covering the nasal septum and the lateral wall, delivering energy from an energy delivery member attached to or inside of the inflatable balloon, and removing the reshaping device from the nasal airway.

6 Claims, 9 Drawing Sheets

Related U.S. Application Data continuation-in-part of application No. 15/480,575, filed on Apr. 6, 2017, now Pat. No. 10,028,780, which is a continuation of application No. 15/380,812, filed on Dec. 15, 2016, now Pat. No. 9,913,682, which is a continuation of application No. 14/963,719, filed on Dec. 9, 2015, now Pat. No. 9,526,571, which is a continuation of application No. 13/495,879, filed on Jun. 13, 2012, now Pat. No. 9,237,924.

(60) Provisional application No. 61/603,864, filed on Feb. 27, 2012, provisional application No. 61/496,930, filed on Jun. 14, 2011.

(51) Int. Cl.
| | |
|---|---|
| *A61B 18/08* | (2006.01) |
| *A61B 18/06* | (2006.01) |
| *A61B 18/14* | (2006.01) |
| *A61N 5/06* | (2006.01) |
| *A61N 5/02* | (2006.01) |
| *A61F 5/56* | (2006.01) |
| *A61B 18/16* | (2006.01) |
| *A61B 17/28* | (2006.01) |
| *A61N 1/40* | (2006.01) |
| *A61F 7/10* | (2006.01) |
| *A61B 5/01* | (2006.01) |
| *A61F 5/08* | (2006.01) |
| *A61B 18/02* | (2006.01) |
| *A61B 18/00* | (2006.01) |
| *A61B 18/18* | (2006.01) |
| *A61B 18/20* | (2006.01) |
| *A61B 17/32* | (2006.01) |
| *A61N 7/02* | (2006.01) |
| *A61B 18/04* | (2006.01) |
| *A61M 25/10* | (2013.01) |

(52) U.S. Cl.
CPC ............ *A61B 18/06* (2013.01); *A61B 18/085* (2013.01); *A61B 18/12* (2013.01); *A61B 18/1206* (2013.01); *A61B 18/14* (2013.01); *A61B 18/1442* (2013.01); *A61B 18/1445* (2013.01); *A61B 18/1477* (2013.01); *A61B 18/1485* (2013.01); *A61B 18/16* (2013.01); *A61F 5/08* (2013.01); *A61F 5/56* (2013.01); *A61F 7/10* (2013.01); *A61N 1/403* (2013.01); *A61N 5/025* (2013.01); *A61N 5/0603* (2013.01); *A61N 5/0625* (2013.01); *A61B 17/320068* (2013.01); *A61B 18/02* (2013.01); *A61B 18/1815* (2013.01); *A61B 18/20* (2013.01); *A61B 2017/248* (2013.01); *A61B 2018/00005* (2013.01); *A61B 2018/0016* (2013.01); *A61B 2018/0022* (2013.01); *A61B 2018/00023* (2013.01); *A61B 2018/0091* (2013.01); *A61B 2018/00178* (2013.01); *A61B 2018/00327* (2013.01); *A61B 2018/00434* (2013.01); *A61B 2018/00577* (2013.01); *A61B 2018/00595* (2013.01); *A61B 2018/00642* (2013.01); *A61B 2018/00702* (2013.01); *A61B 2018/00708* (2013.01); *A61B 2018/00791* (2013.01); *A61B 2018/00821* (2013.01); *A61B 2018/00875* (2013.01); *A61B 2018/00886* (2013.01); *A61B 2018/00922* (2013.01); *A61B 2018/00928* (2013.01); *A61B 2018/00982* (2013.01); *A61B 2018/00994* (2013.01); *A61B 2018/0212* (2013.01); *A61B 2018/0225* (2013.01); *A61B 2018/0262* (2013.01); *A61B 2018/044* (2013.01); *A61B 2018/126* (2013.01); *A61B 2018/1253* (2013.01); *A61B 2018/143* (2013.01); *A61B 2018/1425* (2013.01); *A61B 2018/1467* (2013.01); *A61B 2018/1807* (2013.01); *A61B 2018/1861* (2013.01); *A61M 2025/105* (2013.01); *A61N 7/022* (2013.01); *F04C 2270/041* (2013.01)

(56) References Cited

U.S. PATENT DOCUMENTS

| | | |
|---|---|---|
| 5,533,499 A | 7/1996 | Johnson |
| 5,542,916 A | 8/1996 | Hirsch et al. |
| 5,624,439 A | 4/1997 | Edwards et al. |
| 5,674,191 A | 10/1997 | Edwards et al. |
| 5,707,349 A | 1/1998 | Edwards |
| 5,718,702 A | 2/1998 | Edwards |
| 5,728,094 A | 3/1998 | Edwards |
| 5,730,719 A | 3/1998 | Edwards |
| 5,733,280 A | 3/1998 | Avitall |
| 5,738,114 A | 4/1998 | Edwards |
| 5,743,870 A | 4/1998 | Edwards |
| 5,743,904 A | 4/1998 | Edwards |
| 5,746,224 A | 5/1998 | Edwards |
| 5,800,429 A | 9/1998 | Edwards |
| 5,807,306 A | 9/1998 | Shapland et al. |
| 5,816,095 A | 10/1998 | Nordell, II et al. |
| 5,817,049 A | 10/1998 | Edwards |
| 5,820,580 A | 10/1998 | Edwards et al. |
| 5,823,197 A | 10/1998 | Edwards |
| 5,827,277 A | 10/1998 | Edwards |
| 5,843,021 A | 12/1998 | Edwards et al. |
| 5,843,077 A | 12/1998 | Edwards |
| 5,846,235 A | 12/1998 | Pasricha et al. |
| 5,879,349 A | 3/1999 | Edwards |
| 5,938,659 A | 8/1999 | Tu et al. |
| 6,045,549 A | 4/2000 | Smethers et al. |
| 6,096,033 A | 8/2000 | Tu et al. |
| 6,102,907 A | 8/2000 | Smethers et al. |
| 6,109,268 A | 8/2000 | Thapliyal et al. |
| 6,126,657 A | 10/2000 | Edwards et al. |
| 6,131,579 A | 10/2000 | Thorson et al. |
| 6,139,546 A | 10/2000 | Koenig et al. |
| 6,152,143 A | 11/2000 | Edwards |
| 6,165,173 A | 12/2000 | Kamdar et al. |
| 6,179,803 B1 | 1/2001 | Edwards et al. |
| 6,210,355 B1 | 4/2001 | Edwards et al. |
| 6,228,079 B1 | 5/2001 | Koenig |
| 6,231,569 B1 | 5/2001 | Bek et al. |
| 6,293,941 B1 | 9/2001 | Strul et al. |
| 6,309,386 B1 | 10/2001 | Bek |
| 6,371,926 B1 | 4/2002 | Thorson et al. |
| 6,383,181 B1 | 5/2002 | Johnston et al. |
| 6,391,028 B1 | 5/2002 | Fanton et al. |
| 6,416,491 B1 | 7/2002 | Edwards et al. |
| 6,425,151 B2 | 7/2002 | Barnett |
| 6,431,174 B1 | 8/2002 | Knudson et al. |
| 6,451,013 B1 | 9/2002 | Bays et al. |
| 6,502,574 B2 | 1/2003 | Stevens et al. |
| 6,551,310 B1 | 4/2003 | Ganz et al. |
| 6,562,036 B1 | 5/2003 | Ellman et al. |
| 6,575,969 B1 | 6/2003 | Rittman et al. |
| 6,589,235 B2 | 7/2003 | Wong et al. |
| 6,659,106 B1 | 12/2003 | Hovda et al. |
| 6,911,027 B1 | 6/2005 | Edwards et al. |
| 6,978,781 B1 | 12/2005 | Jordan |
| 7,055,523 B1 | 6/2006 | Brown |
| 7,097,641 B1 | 8/2006 | Arless et al. |
| 7,114,495 B2 | 10/2006 | Lockwood, Jr. |
| 7,322,993 B2 | 1/2008 | Metzger et al. |
| 7,361,168 B2 | 4/2008 | Makower et al. |
| 7,416,550 B2 | 8/2008 | Protsenko et al. |
| 7,442,191 B2 | 10/2008 | Hovda et al. |
| 7,655,243 B2 | 2/2010 | Deem et al. |
| 7,678,069 B1 | 3/2010 | Baker et al. |
| 7,780,730 B2 | 8/2010 | Saidi |
| 7,824,394 B2 | 11/2010 | Manstein |

(56) References Cited

U.S. PATENT DOCUMENTS

| | | |
|---|---|---|
| 7,850,683 B2 | 12/2010 | Elkins et al. |
| 7,997,278 B2 | 8/2011 | Utley et al. |
| 8,114,062 B2 | 2/2012 | Muni et al. |
| 8,128,617 B2 | 3/2012 | Bencini et al. |
| 8,137,345 B2 | 3/2012 | McNall, III et al. |
| 8,317,781 B2 | 11/2012 | Owens et al. |
| 8,317,782 B1 | 11/2012 | Ellman et al. |
| 8,936,594 B2 | 1/2015 | Wolf et al. |
| 8,986,301 B2 | 3/2015 | Wolf et al. |
| 9,027,597 B2 | 5/2015 | Kubo |
| 9,072,597 B2 | 7/2015 | Wolf et al. |
| 9,125,677 B2 | 9/2015 | Sobol et al. |
| 9,179,964 B2 | 11/2015 | Wolf et al. |
| 9,179,967 B2 | 11/2015 | Wolf et al. |
| 9,237,924 B2 | 1/2016 | Wolf et al. |
| 9,247,989 B2 | 2/2016 | Truckai |
| 9,415,194 B2 | 8/2016 | Wolf et al. |
| 9,433,463 B2 | 9/2016 | Wolf et al. |
| 9,452,010 B2 | 9/2016 | Wolf et al. |
| 9,452,087 B2 | 9/2016 | Holm et al. |
| 9,486,278 B2 | 11/2016 | Wolf et al. |
| 9,526,571 B2 | 12/2016 | Wolf et al. |
| 9,687,288 B2 | 6/2017 | Saadat |
| 9,687,296 B2 | 6/2017 | Wolf et al. |
| 9,763,723 B2 | 9/2017 | Saadat |
| 9,763,743 B2 | 9/2017 | Lin et al. |
| 9,788,886 B2 | 10/2017 | Wolf et al. |
| 9,801,752 B2 | 10/2017 | Wolf et al. |
| 9,888,957 B2 | 2/2018 | Wolf et al. |
| 9,913,682 B2 | 3/2018 | Wolf et al. |
| 9,943,361 B2 | 4/2018 | Wolf et al. |
| 10,028,780 B2 | 7/2018 | Wolf et al. |
| 10,028,781 B2 | 7/2018 | Saadat |
| 10,265,115 B2 | 4/2019 | Wolf et al. |
| 10,335,221 B2 | 7/2019 | Wolf et al. |
| 10,376,300 B2 | 8/2019 | Wolf et al. |
| 10,398,489 B2 | 9/2019 | Wolf et al. |
| 10,456,185 B2 | 10/2019 | Wolf et al. |
| 10,456,186 B1 | 10/2019 | Wolf et al. |
| 10,470,814 B2 | 11/2019 | Wolf et al. |
| 10,485,603 B2 | 11/2019 | Wolf et al. |
| 10,603,059 B2 | 3/2020 | Dinger et al. |
| D880,694 S | 4/2020 | Ng et al. |
| D881,904 S | 4/2020 | Angeles et al. |
| 10,631,925 B2 | 4/2020 | Wolf et al. |
| 10,722,282 B2 | 7/2020 | Wolf et al. |
| 2002/0016588 A1 | 2/2002 | Wong et al. |
| 2002/0049464 A1 | 4/2002 | Donofrio et al. |
| 2002/0087155 A1 | 7/2002 | Underwood et al. |
| 2002/0128641 A1 | 9/2002 | Underwood et al. |
| 2003/0144659 A1 | 7/2003 | Edwards |
| 2003/0208194 A1 | 11/2003 | Hovda et al. |
| 2003/0225403 A1 | 12/2003 | Woloszko et al. |
| 2004/0193238 A1 | 9/2004 | Mosher et al. |
| 2004/0215235 A1 | 10/2004 | Jackson et al. |
| 2004/0220644 A1 | 11/2004 | Shalev et al. |
| 2005/0020901 A1 | 1/2005 | Belson et al. |
| 2005/0119643 A1 | 6/2005 | Sobol et al. |
| 2005/0222565 A1 | 10/2005 | Manstein |
| 2005/0234439 A1 | 10/2005 | Underwood |
| 2005/0240147 A1 | 10/2005 | Makower et al. |
| 2005/0288665 A1 | 12/2005 | Woloszko |
| 2006/0089596 A1* | 4/2006 | Ravo .............. A61M 25/10182 600/4 |
| 2006/0195169 A1 | 8/2006 | Gross et al. |
| 2006/0235377 A1 | 10/2006 | Earley et al. |
| 2006/0253117 A1 | 11/2006 | Tovda et al. |
| 2006/0276817 A1 | 12/2006 | Vassallo et al. |
| 2007/0043350 A1 | 2/2007 | Soltesz et al. |
| 2007/0049999 A1 | 3/2007 | Esch et al. |
| 2007/0066944 A1 | 3/2007 | Nyte |
| 2007/0073282 A1 | 3/2007 | McGaffigan et al. |
| 2007/0093710 A1 | 4/2007 | Maschke |
| 2007/0219600 A1 | 9/2007 | Gertner et al. |
| 2007/0244529 A1 | 10/2007 | Choi et al. |
| 2008/0027423 A1 | 1/2008 | Choi et al. |
| 2008/0027480 A1 | 1/2008 | van der Burg et al. |
| 2008/0082090 A1 | 4/2008 | Manstein |
| 2008/0125626 A1 | 5/2008 | Chang et al. |
| 2008/0154237 A1 | 6/2008 | Chang et al. |
| 2008/0183251 A1 | 7/2008 | Azar et al. |
| 2008/0255642 A1 | 10/2008 | Zarins et al. |
| 2008/0312644 A1 | 12/2008 | Fourkas et al. |
| 2009/0018485 A1 | 1/2009 | Krespi et al. |
| 2009/0124958 A1 | 5/2009 | Li et al. |
| 2009/0143821 A1 | 6/2009 | Stupak |
| 2009/0192505 A1 | 7/2009 | Askew et al. |
| 2009/0292358 A1 | 11/2009 | Saidi |
| 2010/0144996 A1 | 6/2010 | Kennedy et al. |
| 2010/0152730 A1 | 6/2010 | Makower et al. |
| 2010/0160906 A1 | 6/2010 | Jarrard |
| 2010/0174283 A1 | 7/2010 | McNall, III et al. |
| 2010/0204560 A1 | 8/2010 | Salahieh et al. |
| 2010/0241112 A1 | 9/2010 | Watson |
| 2010/0260703 A1 | 10/2010 | Yankelson et al. |
| 2011/0009737 A1 | 1/2011 | Manstein |
| 2011/0118726 A1 | 5/2011 | De La Rama et al. |
| 2011/0282268 A1 | 11/2011 | Baker et al. |
| 2011/0288477 A1 | 11/2011 | Ressemann et al. |
| 2012/0039954 A1 | 2/2012 | Cupit et al. |
| 2012/0078377 A1 | 3/2012 | Gonzales et al. |
| 2012/0298105 A1 | 11/2012 | Osorio |
| 2012/0316473 A1 | 12/2012 | Bonutti et al. |
| 2012/0316557 A1 | 12/2012 | Sartor et al. |
| 2012/0323232 A1* | 12/2012 | Wolf .............. A61B 18/14 606/1 |
| 2013/0053762 A1* | 2/2013 | Rontal .............. A61B 1/015 604/24 |
| 2013/0158536 A1 | 6/2013 | Bloom |
| 2013/0218158 A1 | 8/2013 | Danek et al. |
| 2013/0281997 A1* | 10/2013 | Davie .............. A61B 18/02 606/32 |
| 2014/0114233 A1 | 4/2014 | Deem et al. |
| 2014/0371736 A1* | 12/2014 | Levin .............. A61B 18/082 606/28 |
| 2015/0164571 A1* | 6/2015 | Saadat .............. G01N 29/0618 600/109 |
| 2016/0045277 A1 | 2/2016 | Lin et al. |
| 2016/0121112 A1 | 5/2016 | Azar |
| 2018/0177542 A1 | 6/2018 | Wolf et al. |
| 2018/0263678 A1 | 9/2018 | Saadat |
| 2019/0076185 A1 | 3/2019 | Dinger et al. |
| 2019/0201069 A1 | 7/2019 | Wolf et al. |
| 2019/0231409 A1 | 8/2019 | Wolf et al. |
| 2019/0282289 A1 | 9/2019 | Wolf et al. |
| 2019/0336196 A1 | 11/2019 | Wolf et al. |
| 2019/0343577 A1 | 11/2019 | Wolf et al. |
| 2019/0357927 A1* | 11/2019 | Palushi .............. A61M 29/02 |
| 2020/0100829 A1 | 4/2020 | Wolf et al. |
| 2020/0129223 A1 | 4/2020 | Angeles et al. |
| 2020/0170699 A1 | 6/2020 | Wolf et al. |
| 2020/0205884 A1 | 7/2020 | Wolf et al. |

FOREIGN PATENT DOCUMENTS

| | | |
|---|---|---|
| WO | 2001043653 | 6/2001 |
| WO | 2003024349 A1 | 3/2003 |
| WO | 2007037895 A2 | 4/2007 |
| WO | 2007134005 A1 | 11/2007 |
| WO | 2010077980 A1 | 7/2010 |
| WO | 2012174161 A1 | 12/2012 |
| WO | 2013028998 A2 | 2/2013 |
| WO | 2014022436 A1 | 2/2014 |
| WO | 2015047863 A1 | 4/2015 |
| WO | 2015048806 A2 | 4/2015 |
| WO | 2015153696 A1 | 10/2015 |

OTHER PUBLICATIONS

Buckley et al., "Mapping the depth dependence of shear properties in articular cartilage," J Biomech., 41(11):2430-2437, Epub Jul. 10, 2008.

(56) References Cited

OTHER PUBLICATIONS

Chen et al., China Journal of Endoscopy, vol. 11, No. 3. pp. 239-243, Mar. 2005, [English Translation of Title] "Radiofrequency treatment of nasal posterior-under nerve ethmoidal nerve and infraturbinal for perennial allergic rhinitis under nasal endoscope," [also translated as] "Preliminary exploration of radiofrequency thermocoagulation of the posterior inferior nasal nerve, anterior ethmoidal nerve, and inferior nasal concha under nasal endoscopy in the treatment of perennial allergic rhinitis." 9 pages.
Cole, "Biophysics of nasal airflow: a review," Am J Rhinol., 14(4):245-249, Jul.-Aug. 2000.
Cole, "The four components of the nasal valve," Am J Rhinol., 17(2):107-110, Mar.-Apr. 2003.
Extended European Search Report for Application No. 19159707.9, dated Nov. 9, 2019, 7 pages.
Fang et al., J First Mil Med Univ, vol. 25 No. 7, pp. 876-877, 2005, [English translation of title] "Nasal endoscopy combined with multiple radiofrequency for perennial allergic rhinitis" [also translated as] "Nasal Endoscopic Surgery Combined with Multisite Radiofrequency Technology for Treating Perennial Allergic Rhinitis," 4 pages.
Griffin et al., "Effects of enzymatic treatments on the depth-dependent viscoelastic shear properties of articular cartilage," J Orthop Res., 32(12):1652-1657, Epub Sep. 5, 2014.
International Search Report and Written Opinion for PCT/US2012/042316, dated Aug. 24, 2012, 15 pages.
International Search Report and Written Opinion for PCT/US2014/054726, dated Dec. 23, 2014, 5 pages.
International Search Report and Written Opinion for PCT/US2015/023742, dated Jun. 29, 2015, 5 pages.
Kjaergaard et al., "Relation of nasal air flow to nasal cavity dimensions," Arch Otolaryngol Head Neck Surg., 135(6):565-570, Jun. 2009.
Kong et al., Journal of Clinical Otorhinolaryngology, 2005. "Clinical observation on radiofrequency ablation treatment in perennial allergic rhinitis," Retrieved from the Internet: <URL:http://en.cnki.com.cn/Article_en/CJFDTOTAL-LCEH200505015.htm>, 1 page.
Liu et al., China Journal of Endoscopy, vol. 14, No. 11, pp. 1127-1130, Nov. 2008, [English Translation of Title] "Impact of treatment of perennial rhinitis by radiofrequency thermocoagulations to vidian and antirior ethomoidal nerves on mucociliary clearance," [also translated as] "Impact of radiofrequency thermocoagulation of bilateral vidian and anterior ethmoidal nerve cluster regions on nasal mucociliary transport function in perennial allergic rhinitis and vasomotor rhinitis." 12 pages.
Silverberg et al., "Structure-function relations and rigidity percolation in the shear properties of articular cartilage," Biophys J., 107(7):1721-1730, Oct. 7, 2014.
Singapore Search Report for Application Serial No. 201309238-2, dated Apr. 17, 2014, 27 pages.
Stewart et al., "Development and validation of the Nasal Obstruction Symptom Evaluation (NOSE) scale," Otolaryngol Head Neck Surg., 130(2):157-163, Feb. 2004.
Stupak, "A Perspective on the Nasal Valve," Dept. of Otorhinolaryngology, Albert Einstein College of Medicine, Nov. 6, 2009.
Stupak, "Endonasal repositioning of the upper lateral cartilage and the internal nasal valve," Ann Otol Rhinol Laryngol., 120(2):88-94, Feb. 2011.

* cited by examiner

METHODS AND DEVICES TO TREAT NASAL AIRWAYS

CROSS-REFERENCE TO RELATED APPLICATIONS

This application is a continuation of U.S. Non-Provisional application Ser. No. 16/041,101, filed Jul. 20, 2018, now U.S. Pat. No. 10,722,282, which is a continuation-in-part of U.S. Non-Provisional application Ser. No. 15/480,575 filed Apr. 6, 2017, now U.S. Pat. No. 10,028,780, which claims benefit U.S. Non-Provisional application Ser. No. 15/380,812, filed Dec. 15, 2016, now U.S. Pat. No. 9,913,682, which claims benefit of U.S. Non-Provisional application Ser. No. 14/963,719, filed Dec. 9, 2015, now U.S. Pat. No. 9,526,571, which claims benefit of U.S. Non-Provisional application Ser. No. 13/495,879, filed Jun. 13, 2012, now U.S. Pat. No. 9,237,924, which claims the benefit of U.S. Provisional Application No. 61/496,930, filed Jun. 14, 2011, and U.S. Provisional Application No. 61/603,864, filed Feb. 27, 2012. The disclosures of all of the above-referenced applications are hereby incorporated by reference in their entireties.

FIELD

This application describes medical devices, systems and methods for treating structures in the human airway, to facilitate breathing, reduce chronic runny nose or address any of a number of other airway conditions.

BACKGROUND

During respiration, the anatomy, shape, tissue composition and properties of the human airway produce airflow resistance. The nose is responsible for almost two thirds of this resistance. Most of the resistance occurs in the anterior part of the nose, known as the internal nasal valve, which acts as a flow-limiter. Although this flow-limiting effect of the internal nasal valve works well in most people, a large number of people have a poorly functioning nasal valve, which results in too much resistance to breathing and thus respiration abnormalities, which can significantly affect a patient's quality of life.

The internal nasal valve area is formed by the nasal septum, the caudal border of the upper lateral cartilage (ULC), the head of the inferior turbinate, and the pyriform aperture and tissues that surround it. The angle formed between the caudal border of the ULC and the nasal septum is normally about 10-15 degrees, as illustrated in FIG. 2A. The internal nasal valve is usually the narrowest part of the nasal airway and is responsible for more than two thirds of the airflow resistance produced by the nose. Inadequate nasal valve structural strength, stiffness or conformation can be a consequence of previous surgery, trauma, aging, and/or primary weakness of the upper lateral cartilage.

Poor nasal airflow can also occur in people with a structurally normal nasal/nasal valve anatomy, as well as a normal nasal passage cross-sectional area. The strength, structure and resistance to collapse of the nasal passage can also be normal in people with poor nasal airflow. People can have poor nasal airflow from other causes, including deviated septum, allergic rhinitis (runny nose), non-allergic rhinitis, turbinate hyperplasia, nasal tip ptosis, and nasal polyposis (nasal polyps). Regardless of the cause, poor nasal breathing and/or nasal congestion has profound effects on a person's health and quality of life.

Existing methods for correcting nasal valve inadequacy include surgically repositioning the upper lateral cartilage or adding structural grafts to support the lateral wall of the nose. Surgical structural enhancement of the valve can include the use of grafts made from cartilage or any of a number of other materials. The most frequent methods involve surgical implantation of spreader grafts between the upper lateral cartilage and the nasal septum. Alternately, stents, spreaders or other devices may be implanted to reposition the ULC. Although they work in some cases, invasive surgical and implant solutions may also involve substantial risk and post-surgical discomfort.

Another attempted solution to nasal valve insufficiency involves the use of external (non-implanted) nasal dilators, placed temporarily and removed by the patient. Such external devices, such as the "Breathe Right" strip, are placed on the outside surface of the nose. Example of such devices are described in U.S. Pat. Nos. 5,533,499 and 7,114,495. Other devices may be temporarily placed in the nasal cavity but not surgically implanted, for example the devices described in U.S. Pat. Nos. 7,055,523 and 6,978,781. These temporary devices, whether external or internal, can be uncomfortable, unsightly, cause skin irritation, and require frequent removal and replacement by the patient.

The assignee of the present application has developed devices, systems and methods for treating the upper airway to ameliorate nasal valve insufficiency, runny nose and/or other conditions. Further description of these devices, systems and methods may be found, for example, in the patents and applications incorporated by reference above. Despite the many advances described in those and other references, improvements and enhancements are still desirable.

BRIEF SUMMARY

Embodiments of the present application are directed to devices, systems and methods for treating nasal airways. Such embodiments may be used to improve breathing by decreasing airflow resistance or perceived airflow resistance in the nasal airways. For example, the devices, systems and methods described herein may be used to reshape, remodel, strengthen, or change the properties of the tissues of the nose, including, but not limited to the skin, muscle, mucosa, submucosa and cartilage in the area of the nasal valves. These or alternative embodiments may alternatively or additionally be used to deliver energy to nasal airway tissues, for example to help reshape the tissues and/or to ablate goblet cells, nerve fibers or other tissue, to reduce rhinitis.

According to one aspect of the disclosure, a method for reshaping a nasal airway in a patient may involve: advancing an inflatable balloon of a reshaping device in an uninflated configuration into a nostril of the patient and between a nasal septum and a lateral wall of the nasal airway; inflating the inflatable balloon to an inflated configuration to cause the inflatable balloon to contact nasal mucosa covering the nasal septum and the lateral wall; delivering energy from an energy delivery member attached to or inside of the inflatable balloon; and removing the reshaping device from the nasal airway. In one embodiment, inflating the inflatable balloon deforms the nasal septum and/or the lateral wall, and a diameter of the nasal airway remains expanded after removal of the reshaping device and healing of the lateral wall. In some embodiments, the inflatable balloon is positioned between an upper portion of the nasal septum and the lateral wall, and the inflatable balloon is inflated until a nasal valve angle of the nasal airway reaches a desired size. In some embodiments, inflating the inflatable balloon applies sufficient force to a nasal turbinate to deform and break bone in the nasal turbinate.

The energy delivery member may be any suitable energy delivery member or combination of members. In one embodiment a radiofrequency member is attached to an outer surface of the inflatable balloon. For example, the radiofrequency member may be a single monopolar electrode, multiple monopolar electrodes, or multiple bipolar electrodes. In some embodiments, delivering the energy involves delivering radiofrequency energy via the radiofrequency member and introducing plasma into the inflatable balloon. In some embodiments, the energy delivery member is a wire mesh attached to an outer surface of the inflatable balloon. In other embodiments, the energy delivery member comprises heated fluid inside the inflatable balloon, and the inflating and the delivering steps of the method are performed as one step comprising inflating the inflatable balloon with the heated fluid.

In some embodiments, delivering the energy involves delivering sufficient energy to damage nerve fibers underlying the nasal mucosa. In some embodiments, delivering the energy to damage the nerve fibers involves ablating at least one targeted nerve. For example, the targeted nerve may be the sphenopalatine ganglion and/or a branch of the sphenopalatine ganglion. According to various alternative embodiments, any suitable type of energy may be delivered by the energy delivery member, such as but not limited to radiofrequency, ultrasound, microwave, heat, electrical, light and laser energy.

In some embodiments, the method may further include maintaining the inflatable balloon in the inflated configuration in the nasal airway for a period of time to allow a pharmaceutical substance coated on or contained within the inflatable balloon to leave the inflatable balloon and enter the nasal mucosa. For example, the pharmaceutical substance might be a steroid. In other embodiments, the patient is suffering from a nosebleed, and the method further includes maintaining the inflatable balloon in the inflated configuration in the nasal airway for a period of time to stop the nosebleed.

In another aspect of the present disclosure, a method of treating a patient's nasal airway may involve positioning an inflatable balloon within the nasal airway adjacent to a nasal tissue to be treated, inflating the inflatable balloon to an inflated configuration, to apply sufficient force to the nasal tissue to alter a shape of the nasal tissue, maintaining the inflatable balloon in the inflated configuration in the nasal airway for a period of time, deflating the inflatable balloon, and removing the inflatable balloon from the nasal airway. The nasal tissue will at least partially maintain the altered shape after the treating element is removed and the nasal tissue heals. In some embodiments, the method may further involve delivering energy from the inflatable balloon during at least part of the maintaining step.

In another aspect of the present disclosure, a method for treating a nasal airway in a patient involves advancing an inflatable balloon in an uninflated configuration into the nasal airway, inflating the inflatable balloon to an inflated configuration to cause the inflatable balloon to contact nasal mucosa lining the nasal airway, delivering energy from the inflatable balloon to damage nerve fibers underlying the nasal mucosa, deflating the inflatable balloon, and removing the inflatable balloon from the nasal airway.

In some embodiments, the energy is delivered from an energy delivery member comprising a radiofrequency member attached to an outer surface of the inflatable balloon. In some embodiments, delivering the energy involves delivering radiofrequency energy via the radiofrequency member and introducing plasma into the inflatable balloon.

In another aspect of the present disclosure, a system for treating a nasal airway in a patient may include a treatment device and a controller and a power supply coupled with the treatment device. The treatment device includes a treatment element including an inflatable balloon and an energy delivery member coupled with the energy delivery balloon. The inflatable balloon is configured to be advanced into the nasal airway in an uninflated configuration and then inflated to assume an inflated configuration. The device also includes a shaft attached to a proximal end of the treatment element and a handle attached to a proximal end of the shaft.

In some embodiments, the energy delivery member is a wire mesh attached to an outer surface of the inflatable balloon. The energy delivery member (or members) may deliver any suitable type of energy, such as but not limited to radiofrequency, ultrasound, microwave, heat, electrical, light and laser energy. In some embodiments, a pharmaceutical substance may be coated on, or contained within, the inflatable balloon. In some embodiments, the shaft may include an outer shaft and an inner shaft that extends through an interior of the inflatable balloon. A proximal end and a distal end of the inflatable balloon are attached to the inner shaft, and the inner shaft includes an inflation lumen and at least one inflation aperture for inflating the inflatable balloon. According to various embodiments, the controller and/or the power source may be located in the handle or may be separate from the handle, for example in a separate box or, in the case of the power source, the system may include a cord for plugging into a wall socket.

According to one aspect, a device for treating a patient's nasal airway is provided. In one embodiment, the device comprises an energy delivery element sized to be inserted into a nose or to be delivered external to a nose. The energy delivery element is configured to deliver energy to tissues within the nose and to reshape a region of the nose to a new conformation.

According to one embodiment, a device for treating a patient's nasal airway comprises an elongate shaft having a proximal end and a distal end. The device further comprises a handle at the proximal end of the elongate shaft. The device also comprises a treatment element at the distal end of the elongate shaft. The treatment element is sized to be inserted into the nasal airway or to be delivered external to a nose. The treatment element is configured to reshape a region of the nose to a new conformation and comprises an electrode configured to deliver radiofrequency (RF) energy to the nasal tissue.

Other embodiments of devices for treating a patient's nasal airway include devices that apply other types of treatment. For example, a treatment device may apply energy in the form selected from the group consisting of ultrasound, microwave, heat, radiofrequency, electrical, light and laser. The treatment device may also be configured to inject a polymerizing liquid or to deliver a cauterizing agent to nasal tissue. Other embodiments are described below.

The devices described herein may be configured to be positioned internally within the nose, external to the nose, or both. Certain embodiments are configured to be delivered into one nostril, and other embodiments are configured to be delivered into both nostrils. In some embodiments the device may comprise a reshaping element having a shape configured to alter a conformation of a region of the nose to a new conformation. For embodiments using an energy delivery element, the reshaping element may be a separate element from the energy delivery element, or the energy delivery element and the reshaping element may be part of the same element. The energy delivery element and/or reshaping element in one embodiment may have a convex shape to create a concavity in nasal tissue.

In embodiments using energy delivery, a handle may be provided comprising a button or other input control to activate one or more electrodes. Electrodes may comprise one or more monopolar needles, one or more monopolar plates, or one or more bipolar electrode pairs (which may also comprise one or more needles or plates). These electrodes may be located in various locations, for example, inside the nasal passageway, external to the nose or both. For example, when using bipolar electrode pairs, a first electrode surface may be positioned internal to the nose and a second electrode surface may be positioned external to the nose, so that the two electrode surfaces are positioned on opposite sides of nasal tissue.

The device of one energy delivery embodiment may comprise an adaptor configured to be connected to an energy source, such as an RF energy source. The device may also comprise a control system configured to control the characteristics of energy applied to tissue. A thermocouple or other sensor may be provided to measure a temperature near tissue or other tissue or device parameter.

In another aspect, a system is provided comprising a device as described above and further below in combination with one or more other components. One such component may be an energy source, such as an RF energy source. Another component may be a control system for controlling the energy source and/or treatment device. In another embodiment, the device or system may comprise a cooling mechanism to cool desired tissue locations while treatment is being applied. In monopolar electrode embodiments, a grounding pad may also be provided as part of the system. Another system includes a positioning device that may be used pre-treatment to determine the optimal device and positioning and/or other parameters for using the device to treat the nasal airway.

According to another aspect, a method of treating a patient's nasal airway is provided. In one embodiment, the method comprises alerting a structure, shape or conformation of one or more nasal structures in an area of a nasal valve by applying a treatment sufficient to modify, by reshaping, tissue at or adjacent to the nasal valve.

According to one embodiment, a method of treating a patient's nasal airway comprises positioning a treatment element within the nasal airway adjacent to nasal tissue to be treated. The treatment element comprises one or more electrodes, such as described above and in further detail below. The method further comprises deforming the nasal tissue into a desired shape by pressing a surface of the treatment element against the nasal tissue to be treated. The method further comprises delivering radiofrequency (RF) energy to the one or more electrodes to locally heat the nasal tissue, wherein delivering RF energy while deforming the nasal tissue causes the nasal tissue to change shape. The method also comprises removing the treatment element from the nasal airway.

The methods, devices and systems described herein may be used to reshape tissue without a surgical incision or implant. In certain embodiments, the reshaping of tissue may be accomplished by ablating tissue. In other embodiments, the reshaping of tissue is accomplished without ablation of tissue. In one embodiment, a treatment element is positioned within a nasal passageway. The treatment element may be used to simultaneously mechanically alter the shape of the internal or external nasal valve and apply treatment to tissue of the nose. The treatment applied may comprise modifying a nasal structure in a manner that increases a volumetric airflow rate of air flowing from an exterior of the patient's body into the patient's nasopharynx without changing a shape of an internal nasal valve. This may involve modifying a mechanical property of a nasal valve. A positioning element may be used to determine a desired position of a treatment element before the treatment element is delivered to the nasal tissue.

The treatment may involve delivering energy in the form of ultrasound, microwave, heat, radiofrequency, electrical, light or laser. The nasal tissue to be treated may be cooled prior to, during or after delivering energy. Delivering energy may comprise measuring a temperature near nasal tissue to be treated, and adjusting a level of energy delivered to the tissue. When RF or other types of energy are used, the energy may be delivered to at least one of the nasal valve, tissue near the nasal valve, or the upper lateral cartilage of tissue. For example, RF energy or other energy may be delivered to the one or more electrodes for about 15 seconds to about 1 minute. RF energy or other energy may be delivered to heat an area of tissue to a temperature of about 50° C. to about 70° C. Other methods not using energy delivery include injecting a polymerizing liquid, delivering a cauterizing agent, or other embodiments described below. Energy or treatment may be delivered for a sufficient period of time or in a sufficient quantity to cause a desired effect. For example, the treatment may cause stress relaxation in the nasal tissue without weakening the tissue. The treatment may also be applied to injure a tissue to be reshaped.

These and other aspects and embodiments of the disclosure are described in greater detail below, in reference to the attached drawing figures.

DETAILED DESCRIPTION

Figure 1:
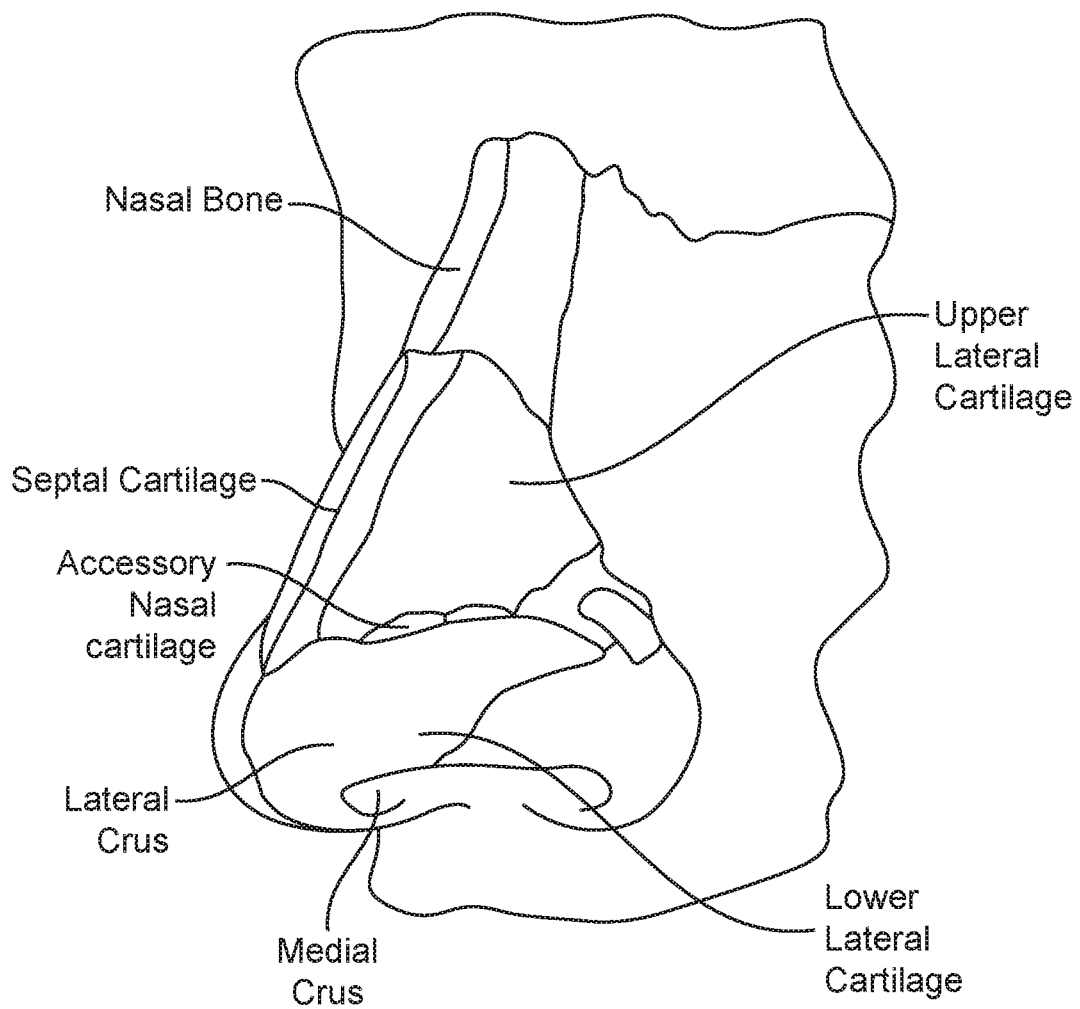
FIG. 1 is a perspective view, anatomical illustration of bone and cartilage structures of a human nose.

The following disclosure describes various embodiments of devices, systems and methods for improving breathing. In some embodiments, breathing may be improved by decreasing airflow resistance or perceived airflow resistance at or near a site of an internal or external nasal valve. Such embodiments may include methods and devices for reshaping, remodeling, strengthening, or otherwise changing the properties of the tissues of the nose, including but not limited to skin, muscle, mucosa, submucosa, and/or cartilage in the area of the nasal valves. Other embodiments may improve breathing via other mechanisms, such as decreasing rhinitis, decreasing mucus production or the like.

In some instances, the devices and methods described in this application may be used to improve nasal breathing in patients with abnormal nasal anatomy. In other examples, however, patients may be treated, and their breathing improved, even if they have normal nasal anatomy, by decreasing nasal airflow resistance in the nasal valve and associated nasal anatomy. Remodeling or changing the structure of the nasal valve can improve nasal airflow in people with inadequate nasal airflow resulting from causes other than nasal valve dysfunction, such as deviated septum, enlarged turbinates, mucosal swelling, and/or mucus overproduction. The methods and devices described herein may be used to treat any of a large number of airway-related conditions, such as chronic rhinitis, snoring, sleep disordered breathing, perceived nasal congestion and poor quality of life, by treating structures within the nose that form the passageways for airflow. Methods and devices described herein may be used to treat nasal airways without the need for more invasive surgical procedures.

FIGS. 1 and 2A-C illustrate anatomical elements of a human nose. The lower lateral cartilage (LLC) includes an external component referred to as the lateral crus and an internal component referred to as the medial crus. The medial crus and septal nasal cartilage create a nasal septum that separates the left and right nostrils. Upper lateral cartilage lies between the lower lateral cartilages and the nasal bone. The left ULC is separated from the right ULC by the septal cartilage extending down the bridge of the nose. The opposing edges of the LLC and ULC may move relative to one another. Disposed between the opposing edges is an accessory nasal cartilage. The septal nasal cartilage and the ULC form an angle (marked as Theta in the drawings) called the nasal valve angle.

Figure 2A:
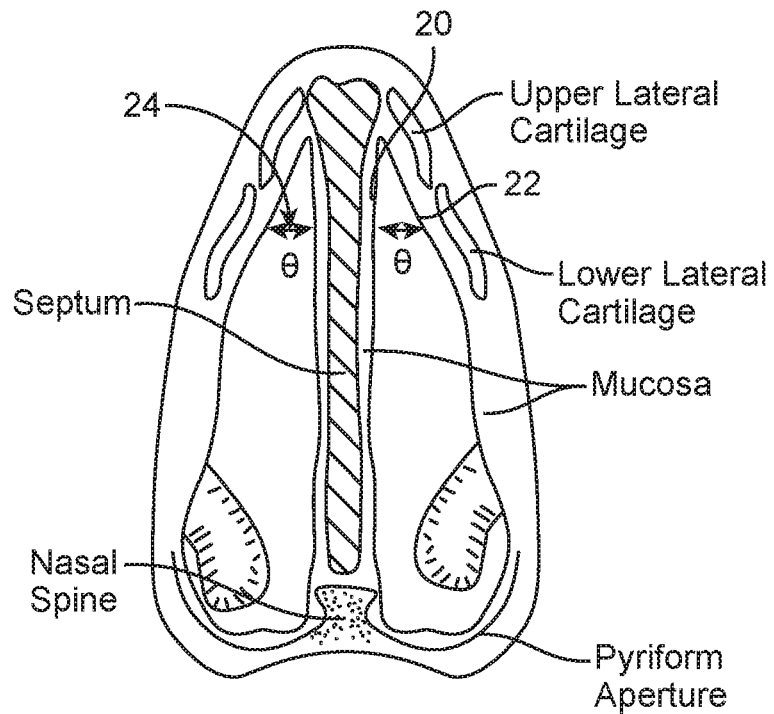
FIG. 2A is a front, cross-sectional view of tissues and structures of a human nose.
Figure 2B:
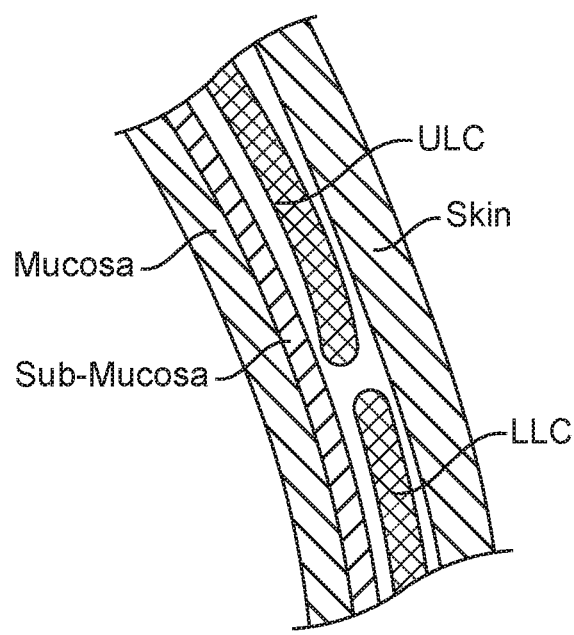
FIG. 2B is a detailed cross-sectional view of a portion of the nose structures of FIG. 2A.

FIG. 2B illustrates a detailed cross-section of a segment of nose tissue in the area of the intersection of the ULC and the LLC. As shown in FIG. 2B, both inner and outer surfaces of the nasal cartilage are covered with soft tissue including mucosa, sub-mucosa and skin.

Figure 2C:
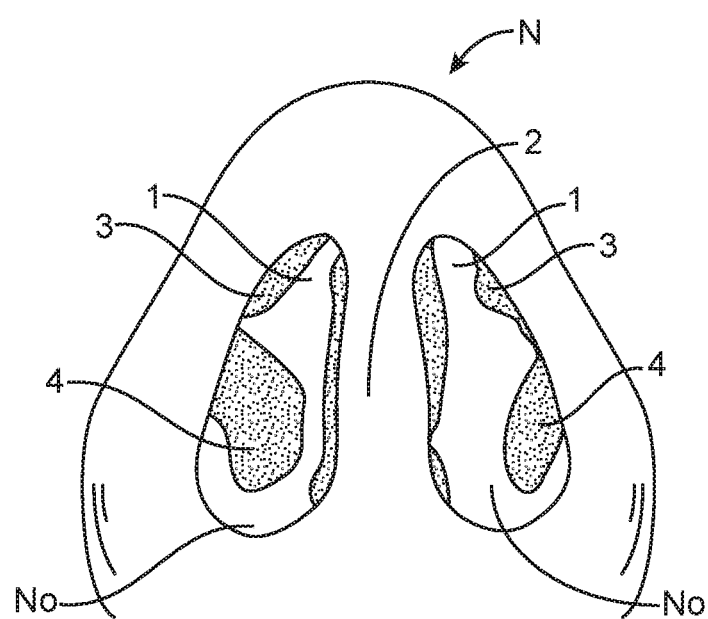
FIG. 2C is a bottom view of a human nose, showing the nostrils, tissues and structures of a human nose.

FIG. 2C illustrates a bottom view of a nose N, looking up into the nostrils NO. FIG. 2C depicts the nasal valves 1, which are located between the nasal septum 2 and the upper lateral cartilage 3. FIG. 2C also shows two of the nasal turbinates 4. The internal nasal valve area 1 of the nasal airway passage NO can be visualized prior to and/or during any treatment by any suitable method, including but not limited to direct visualization, endoscopic visualization, visualization by the use of a speculum, transillumination, ultrasound, MRI, X-ray or any other method. In some embodiments, treatments of the nasal valve area 1 may be performed in conjunction with, or following, another procedure (e.g., a surgical procedure, such as surgically repairing a deviated septum). In such embodiments, the nasal valve area 1 may be visualized and accessed during surgery. In some embodiments, it may be desirable to visualize the internal nasal valve 1 with minimum disturbance, to avoid incorrect assessments due to altering the shape of the nasal valve during visualization. In some embodiments, visualization elements may be incorporated into or combined with treatment devices configured for treating internal and/or external nasal valves.

Airflow through the nasal passage can be measured prior to and/or during any treatment by any suitable method, including, but not limited to, a nasal cannula connected to a pressure measurement system, rhinomanometry, or a rhinohygrometer. Nasal airflow and resistance can also be evaluated by subjective evaluation before and after a manipulation to increase the cross-sectional area of the nasal passage, such as the Cottle maneuver. In some embodiments, it may be desirable to measure nasal airflow and/or resistance prior to, during and/or after a procedure.

The internal nasal valve area of the nasal airway passage can be accessed through the nares. In some embodiments, one or more devices may be used to pull the tip of the nose caudally and increase the diameter of the nares in order to further facilitate access to the internal nasal valve for treatment. Such devices may include speculum type devices and retractors. In other embodiments, access to the internal nasal valve may also be achieved endoscopically via the nares, or via the mouth and throat. In some embodiments, visualization devices may be incorporated or combined with treatment devices for treating internal and/or external nasal valves. These and any other access and/or visualization devices may be used with any of the methods and devices below.

Some embodiments below provide apparatus and methods for increasing the area of the opening at the nasal valve and/or treating nasal valve insufficiency by modifying the structure and/or structural properties of tissues at or adjacent to the internal and/or external nasal valve. Other embodiments below provide apparatus and methods for treating nasal valve insufficiency and/or increasing the area of the opening at nasal valve by reshaping structures within and/or adjacent to an internal and/or external nasal valve to achieve a more optimum shape and minimize or remove airflow obstructions. Still other embodiments combine the two approaches of reshaping and modifying tissue and structures of and adjacent to the internal and/or external nasal valves. Still other embodiments provide apparatus and methods for increasing the area of the opening at the nasal valve and treating nasal obstruction resulting from causes other than nasal valve restriction or insufficiency by improving the structure or function of the nasal valve tissue to increase airflow, for example by strengthening cartilage, whether or not its shape is changed.

Still other embodiments provide apparatus and methods for decreasing airflow resistance in a structurally normal nasal valve and/or increasing the area of the opening at the nasal valve by reshaping structures within and/or adjacent to an internal and/or external nasal valve to achieve a more optimum shape and minimize or remove airflow obstructions. For example, patients having a normal nasal valve anatomy may still benefit from the devices and treatments described herein, as improvement in the nasal valve structure and/or increasing the area of the opening at the nasal valve may improve breathing problems caused by other conditions. Still other embodiments provide for structural changes in the nasal cavity and airway that improve the relative positions of the structures of the nasal cavity to improve nasal breathing. For example, some embodiments may change the shape of, or even break one or more portions of, the nasal turbinates. Other embodiments may move the nasal septum, for example pushing aside a deviated nasal septum. Other embodiments may move soft tissue.

In some embodiments, airflow restrictions to the internal nasal valve may be the result of a smaller-than-optimal internal nasal valve angle 24 (FIG. 2A, i.e., the angle formed between the caudal border of the ULC and the nasal septum). An internal nasal valve angle 24 of less than the normally optimal range of between about 10°-15° can result in airflow restrictions. Thus, in some embodiments, treatments may be designed to reshape structures at or adjacent to the internal nasal valve in order to increase the internal nasal valve angle sufficiently that after such treatments, the nasal valve angle falls within the optimal range of 10-15 degrees. In some embodiments, the internal valve angle may also be increased to be greater than 15 degrees.

An internal nasal valve with a less than optimal area can result in airflow restrictions. Thus, in some embodiments, treatments may be designed to reshape structures at or adjacent to the internal nasal valve, to increase the internal nasal valve angle sufficiently so that after such treatments, the area of the nasal valve falls within an optimal range. In some embodiments, increasing the area of the opening at the nasal valve without increasing the angle of the nasal valve may improve airflow. In some embodiments, increasing the angle of the nasal valve without increasing the area of the opening at the nasal valve may improve airflow. In some embodiments, both the opening at the area of the nasal valve and the angle of the nasal valve may be increased to improve airflow.

Although many of the embodiments and aspects described herein are directed toward modifying tissue in some way to affect airflow through a nasal valve, alternative embodiments, or in some cases the same embodiments, may be used to address other airway conditions or issues. For example, in one embodiment, the device and method may be used to ablate one or more nerve fibers in the airway to reduce mucus hypersecretion and thus help treat rhinitis. The same or other embodiments may be used to ablate goblet cells for the same purpose. In some embodiments, nasal airflow can be increased in the presence of normal nasal valve anatomy and/or normal or enlarged nasal valve angle or area. Thus, the embodiments described herein are not limited to reshaping or otherwise modifying nasal airway tissue in and around the nasal valve.

With reference to FIG. 2A, in some embodiments, the internal valve angle 24 or area may be increased by mechanically pressing laterally outwards against the internal lateral nasal wall. In some embodiments, this outward pressing may be performed by an inflatable balloon (such as those discussed below), which may be positioned between the upper portion of the nasal septum 20 and the outer lateral wall 22 and then inflated, pressing against the lateral nasal wall until the nasal valve angle reaches a desired size. In some embodiments, energy application or other treatments may be applied to substantially fix the reshaped tissue in a desired conformational shape before, during or after applying a mechanical reshaping force (e.g., with the inflatable balloon).

In another embodiment, a reshaping device may be used to expand the diameter of the nasal passage at the site of the internal or external nasal valve. The expansion device can be an inflatable balloon, for example. The expansion can increase the diameter to beyond the normal range, for the diameter to remain expanded after removal of the device and healing of the tissue. In some embodiments, a reshaping device may be used to conformationally change the structure of the internal or external nasal valve anatomy to allow greater airflow without necessarily expanding the diameter of the nasal passage. In alternative embodiments, a reshaping or remodeling device can be used to conformationally change the structure of the nasal airway other than the nasal valve, to cause the cross-sectional or three-dimensional structure of the nasal airway to assume a shape less restrictive to airflow, without widening the nasal valve angle. In some embodiments, the tissue of the internal and/or external nasal valve and/or surrounding tissues may be strengthened or otherwise modified to resist a conformational change in response to the negative pressure of inspiration. In some embodiments, this strengthening may be performed by applying treatments selected to change mechanical or structural properties of the treated tissue. In some embodiments, such treatments may include the application of energy to selected regions of nasal valve and/or surrounding tissues.

In various embodiments, energy may be applied in the form of heat, radiofrequency (RF), laser, light, ultrasound (e.g., high intensity focused ultrasound), microwave energy, electromechanical, mechanical force, cooling, alternating or direct electrical current (DC current), chemical, electrochemical, or others. In alternative embodiments, the nasal valve and/or surrounding tissues may be strengthened through the application of cryogenic therapy, or through the injection or application of bulking agents, glues, polymers, collagen and/or other allogenic or autogenic tissues, or growth agents.

Any one or more of the above energy-application mechanisms may also be used to reshape, remodel, or change mechanical or physiologic properties of structures of a nasal valve or surrounding tissues. For example, in some embodiments, energy may be applied to a targeted region of tissue adjacent to a nasal valve, such that the tissue modification results in a tightening, shrinking or enlarging of such targeted tissues, resulting in a change of shape. In some such embodiments, reshaping of a nasal valve section may be achieved by applying energy without necessarily applying a mechanical reshaping force. For example, energy can be used to selectively shrink tissue in specific locations of the nasal airway that will lead to a controlled conformational change.

In alternative embodiments, strengthening and/or conformation change (i.e., reshaping) of nasal valve tissue to reduce negative pressure during inspiration may include modification of tissue growth and/or the healing and fibrogenic process. For example, in some embodiments energy may be applied to a targeted tissue in the region of the internal nasal valve in such a way that the healing process causes a change to the shape of the nasal valve and/or a change in the structural properties of the tissue. In some embodiments, such targeted energy application and subsequent healing may be further controlled through the use of temporary implants or reshaping devices (e.g., internal stents or molds, or external adhesive strips).

According to various embodiments, energy may be delivered to mucosal tissue (the tissue on the surface of the airway) and/or to any submucosal tissue, including but not limited to cartilage. Energy delivery to submucosal tissue(s) may cause a conformational change and/or a change in the physical properties of the tissue being treated, and it may be accomplished by transferring the energy through one or more tissues, such as the epithelium, mucosa, submucosa, muscle, ligaments, tendon and/or skin. In some embodiments, energy may be delivered to the cartilage and/or other submucosal tissues using needles, probes or microneedles that pass through the epithelium, mucosa, submucosa, muscle, ligaments, tendon and/or skin.

Figure 3:
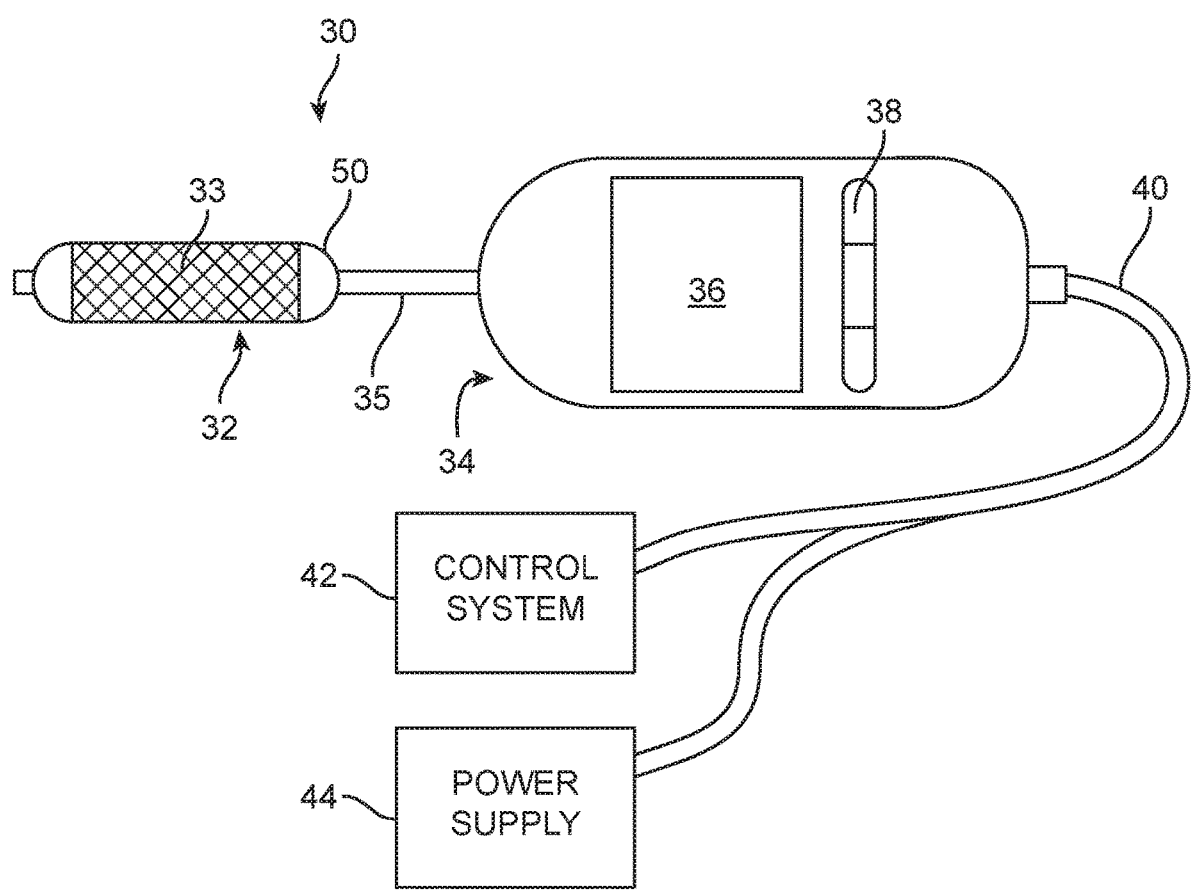
FIG. 3 is a schematic illustration of an upper airway treatment system, according to one embodiment.

FIG. 3 illustrates one embodiment of an upper airway treatment device 30, shown with other components of an upper airway treatment system. The upper airway treatment device 30 includes a treatment element 32, configured to be placed inside a nasal airway to deliver the desired treatment. In some embodiments, the device 30 also includes a handle 34, which may be sized and configured for easy handheld operation by a clinician. The treatment element 32 may be attached to the handle 34 by a shaft 35, which may have varying degrees of rigidity in different embodiments, and which may be malleable in some embodiments. In alternative embodiments, the shaft 35 may be replaced by a flexible catheter. In some embodiments, a display 36 may be provided for displaying information to a clinician during treatment.

In some embodiments, the information provided on the display 36 may include treatment delivery information (e.g., quantitative information describing the energy being delivered to the treatment element) and/or feedback information from sensors within the device and/or within the treatment element. In some embodiments, the display 36 may provide information on physician selected parameters of treatment, including time, power level, temperature, electric impedance, electric current, depth of treatment and/or other selectable parameters.

In some embodiments, the handle 34 may also include input controls 38, such as buttons, knobs, dials, touchpad, joystick, etc. In some embodiments, controls may be incorporated into the display, such as by the use of a touch screen. In further embodiments, the controls 38 and/or the display 36 may be located on an auxiliary device, which may be configured to communicate with the treatment device 30 via analog or digital signals sent over a cable 40 or wirelessly, such as via bluetooth, WiFi (or other 802.11 standard wireless protocol), infrared or any other wired or wireless communication method.

In some embodiments, the treatment system may also include an electronic control system 42, configured to control the timing, location, intensity and/or other properties and characteristics of energy or other treatment applied to targeted regions of a nasal passageway. In some embodiments, the control system 42 may be integrally incorporated into the handle 34. Alternatively, the control system 42 may be located in an external device, which may be configured to communicate with electronics within the handle 34. The controls 38 and/or the display 36 may be located in/on the control system 42 in some embodiments. The control system 42 may include a closed-loop control system having any number of sensors, such as thermocouples, electric resistance or impedance sensors, ultrasound transducers, or any other sensors configured to detect treatment variables or other control parameters.

The treatment system may also include a power supply 44. In some embodiments, the power supply 44 (or a housing for a power supply, such as batteries) may be incorporated into the handle 34 or the control system 42. In alternative embodiments, the power supply 44 may be external to the handle 34. The power supply 44 may be configured to deliver power to the handle 34 and/or the treatment element 32 by a cable or other suitable connection. In some embodiments, the power supply 44 may include a battery or other electrical energy storage or energy generation device. In other embodiments, a power supply may be configured to draw electrical power from a standard wall outlet. In some embodiments, a power supply 44 may also include a system configured for driving a specific energy delivery technology in the treatment element 32. For example, the power supply 44 may be configured to deliver a radio frequency alternating current signal to an RF energy delivery element. Alternatively, the power supply may be configured to deliver a signal suitable for delivering ultrasound or microwave energy via suitable transducers. In further alternative embodiments, the power supply 44 may be configured to deliver a high-temperature or low-temperature fluid (e.g. air, water, steam, saline, or other gas or liquid) to the treatment element 32 by way of a fluid conduit.

In some embodiments, the treatment element 32 may have a substantially rigid or minimally elastic shape, sized and shaped such that it substantially conforms to an ideal shape and size of a patient's nasal passageway, including the internal and external nasal valves. In some embodiments, the treatment element 32 may have a curved shape, either concave or convex with respect to the interior of the lateral wall of the nasal passage. In some embodiments, the shape of a fixed-shape treatment element may be substantially in a shape to be imparted to the cartilage or other structures of the internal or external nasal valve area. Many different embodiments of various treatment elements are described in the patents and applications incorporated herein by reference.

Figure 4A:
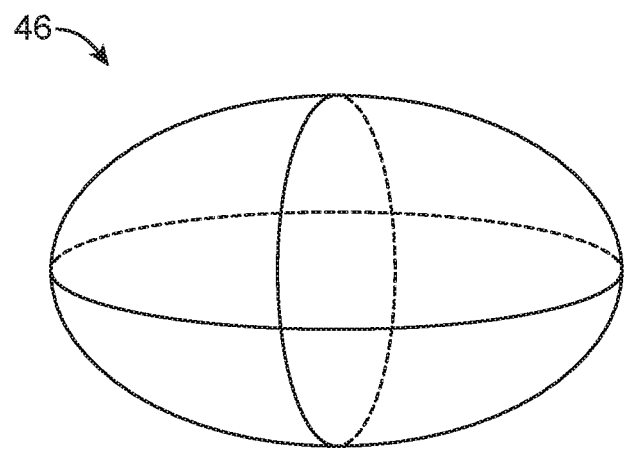
FIG. 4A is a schematic drawing of one possible shape of an inflatable balloon treatment element of an upper airway treatment system, according to one embodiment.
Figure 4B:
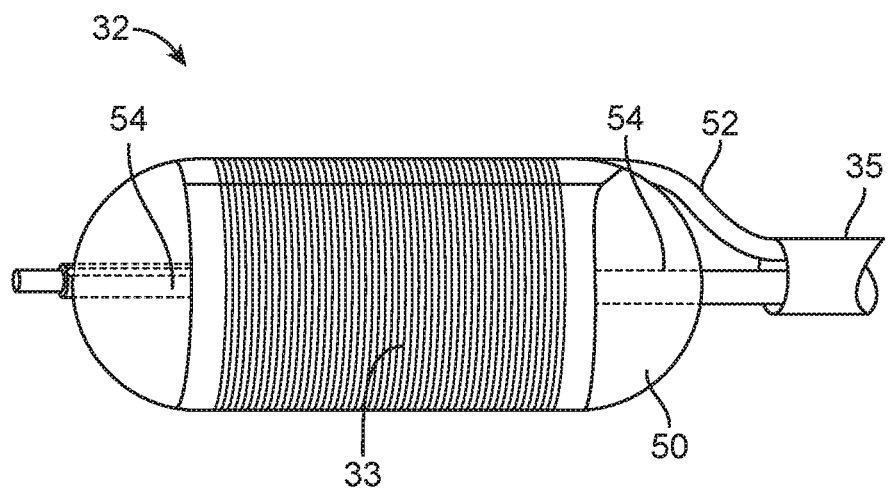
FIG. 4B is a side view of a distal portion of an upper airway treatment system, including an inflatable balloon treatment element, according to one embodiment.

In some embodiments, as shown for example in FIGS. 3 and 4B, the treatment element 32 may include an inflatable balloon 50, with or without one or more energy delivery members 33 attached to it or incorporated into it. The balloon 50 may be made of any suitable inflatable balloon material for medical uses, such as polytetrafluoroethylene (PTFE) or any other balloon polymer. The balloon 50 may also have any suitable shape and size, such as the ellipsoid shape 46 illustrated in FIG. 4A. In some embodiments, for example, the balloon 50 may have an asymmetrical shape, such as an "egg-shape," with a large-diameter proximal end and a smaller-diameter distal end. In some embodiments, the balloon 50 can be shaped to impart a shape to the tissue treated that is conducive to optimal nasal airflow.

FIG. 4B is a side view of a distal portion of the treatment device 30 of FIG. 3, showing the treatment element 32 in greater detail. The treatment element 32 includes the balloon 50 and an energy delivery member 33 disposed over the middle, cylindrical portion of the balloon 50. An inner shaft 54 extends out of the distal end of the outer shaft 35, through the interior of the balloon 50, and out the distal end of the balloon 50. Typically, the balloon 50 is attached at its two ends to the inner shaft 54, and the inner shaft 54 includes an inflation lumen and one or more inflation apertures (not shown) for inflating the balloon 50 with inflation fluid (saline solution, air, water, or any other suitable fluid). The balloon 50 is thus carried on the inner shaft 54 and inflated in the typical manner for a medical/surgical balloon device.

The energy delivery member 33, in this embodiment, is a flexible substrate with a wire mesh that conducts energy supplied by wiring 52, which carries energy from the power supply 44 to the energy delivery member 33. The form of energy delivered by the wire mesh may be, for example, radiofrequency (RF), electrical or heat energy. In various embodiments, the treatment member 32 may be configured to deliver any suitable form of energy, such as but not limited to RF, electrical, heat, microwave, ultrasound, light, laser or cryotherapy (which is actually the removal of energy). Also, alternative variations of the energy delivery member 33 may be located outside, within the wall of, or inside the balloon 50. In some embodiments, for example, energy delivery may be achieved simply by inflating the balloon 50 with a heated or cooled inflation fluid. In such examples, the fluid acts as the energy delivery member. In other embodiments, the treatment element 32 may deliver energy using a combination of mechanisms. For example, in one embodiment, the treatment element 32 may include a monopolar or bipolar RF energy delivery member 33, and the balloon 50 may be inflated with plasma. Any energy delivery mechanism or combination of mechanisms may be used, according to various embodiments.

In some embodiments, the balloon 50 of the treatment element 32 has a width or diameter of about 0.25 inches to about 0.45 inches. In some embodiments, the balloon 50 is about 0.4 inches to about 0.5 inches long. Any suitable size and shape of balloon 50 may be used, according to various embodiments. In some cases, multiple sizes may be provided to a physician user, to allow her to choose a size based on a particular patient's anatomy.

In some embodiments, the shaft 35 has a width or diameter or about 0.235 inches to about 0.25 inches. In some embodiments, the shaft 35 is about 1.5 inches to about 4 inches long. In some embodiments, the shaft 35 and/or handle 34 comprises a polymer, such as polycarbonate or PEEK. In other embodiments, the shaft 35 comprises stainless steel or other metals. The metals may be coated with an external and/or internal insulating coating (e.g., polyester, polyolefin, etc.). The handle 34 may comprise the same material as the shaft 35, in some embodiments. In some embodiments, the shaft 35 is rigid. This may allow a user of the device increased control over the deformation of nasal tissue. In some embodiments, the shaft 35 has some amount of flexibility. This flexibility may allow a user to adjust an angle of the distal tip by bending the distal end of the shaft 35.

In some embodiments, the electrodes or energy delivery member 33 may be made of steel (e.g., stainless, carbon, alloy). Steel may advantageously provide high strength while being low in cost and minimally reactive. In some embodiments, the energy delivery member 33 may be made of materials such as platinum, gold, or silver. Such materials may advantageously provide high conductivity while being minimally reactive. In some embodiments, the energy delivery member 33 may be made of anodized aluminum. Anodized aluminum may advantageously be highly stiff and low in cost. In some embodiments, the energy delivery member 33 may be made of titanium, which may advantageously possess a high strength to weight ratio and be highly biocompatible. In some embodiments, the energy delivery member 33 may be made of nickel titanium alloys. These alloys may advantageously provide high elasticity and be biocompatible. Other similar materials are also possible.

In some embodiments, the balloon 50 may also include an insulating material or one or more insulating sections. These insulating sections may provide an inert portion of the balloon 50 that does not deliver energy to the tissue. In some embodiments, the insulators described herein comprise polyimides or polyamides, which may advantageously possess good dielectric strength and elasticity and be easy to manufacture. In some embodiments, the insulators described herein may be thermoplastic polymers. Thermoplastic polymers may advantageously provide good dielectric strength and high elasticity. In some embodiments, the insulators described herein may be thermoset polymers, which may advantageously provide good dielectric strength and good elasticity. In some embodiments, the insulators described herein may be glass or ceramic infused polymers. Such polymers may advantageously provide good strength, good elasticity, and good dielectric strength.

In some embodiments, the handle 34 and/or shaft 35 may also be made partially or completely of an insulating material (or multiple insulating materials). In some embodiments, the handle 34 and/or shaft 35 is made of a metal, such as stainless steel. In other embodiments, the handle 34 and/or shaft 35 is made of a polymer, such as polycarbonate. Other metals and polymers are also contemplated.

In some embodiments, the treatment device 30 may be used in conjunction with a positioning element (not shown) that can be used to aid in positioning of the treatment element 32. The positioning element may be integrated into the device 30 itself or can be separate. The positioning element may be used to determine the optimal placement of the device to achieve maximal increase in efficacy. In some embodiments, a positioning element is configured to be inserted and manipulated within the nose until the patient reports a desired improvement in breathing. The treatment device 30 may then be used to treat the nasal airway, while the positioning element is holding the nose in the desired configuration. In some embodiments, molds described herein may be used for the same purpose.

In some embodiments, a positioning element comprises a shaft comprising measurement marks indicating depth. For example, a physician may insert this element into the nose to manipulate the tissue to find the depth of treatment at which the patient reports the best breathing experience. The positioning element may comprise marks around the base of the shaft indicating which point of rotation of the device within the nostril provides the best breathing experience. The positioning element may also comprise marks indicating angle of insertion. The physician may then use the measurement marks to guide insertion of the treatment element to the same spot.

The energy delivery member 33 may be used to treat mucosal tissue and/or any suitable submucosal tissue. For example, in some embodiments, energy delivery may be directed toward one or more nerves or nerve fibers located below the mucosal surface, such as but not limited to the sphenopalatine ganglion and any nerves leading into or branching out of the ganglion. In some embodiments, energy may be used to ablate such nerve fibers, to achieve a therapeutic response. For example, in one embodiment, the energy delivery member 33 may be used to ablate the sphenopalatine ganglion to treat chronic rhinitis. In another embodiment, energy may be delivered to a submucosal depth to treat small blood vessels to stop or prevent nosebleeds. In other embodiments, energy may be directed at the mucosa, to shrink the tissue or reduce swelling of the mucosa.

In alternative embodiments, the treatment element 32 may include the balloon 50 without any type of energy delivery member. In such embodiments, the balloon 50 may be used to move, break, rearrange and/or reshape soft tissue and/or bone in the nasal airway. This may be accomplished, for example, by inflating a non-compliant balloon to a desired pressure within the nasal airway. In various embodiments, the balloon 50 may be used to expand the nasal valve, move a lateral wall in a lateral direction, move a nasal septum, break one or more nasal turbinates, flatten or shrink swollen mucosal tissue and/or the like. This may be accomplished, in some embodiments, without delivering energy. In other embodiments, energy may be delivered during and/or after inflation of the balloon 50, to facilitate, expedite or magnify the treatment results.

The inflatable balloon 50 is configured to expand from a collapsed configuration for insertion into the nasal passageway, to an expanded configuration, in which the outer surface of the balloon 50 contacts and engages an internal surface of a nasal passageway. In various embodiments, the balloon 50 may be sized and configured to simply contact the mucosal wall of the nasal cavity, while in other embodiments, the balloon 50 may apply pressure to the mucosal wall. In some cases, this pressure may be sufficient to allow the balloon 50 to move soft tissue, cartilage or bone. In some cases, the balloon 50 may even be used to break bone, such as the bone of one or more nasal turbinates. In some embodiments, an expandable treatment element 32 may comprise an inflation lumen configured to facilitate injection of an inflation medium into an expandable portion of the treatment element 32. In alternative embodiments, an expandable treatment element 32 may comprise one or more segments comprising a shape-memory alloy material (such as Nitinol), which may be configured to expand to a desired size and shape in response to a change of temperature past a transition temperature. In some embodiments, such a temperature change may be brought about by activating an energy-delivery (or removal) element in the treatment element 32.

In some embodiments, the treatment element 32 may expand with various locations on the element expanding to different configurations or not expanding at all to achieve a desired shape of the treatment element. In some embodiments, such expandable treatment elements or sections may be elastic, inelastic, or preshaped. In some embodiments, expandable treatment elements 32 or sections thereof may be made from shape-memory metals, such as nickel-cobalt or nickel-titanium, shape memory polymers, biodegradable polymers or other metals or polymers. The inflatable balloon 50 may be made of any elastic or inelastic expandable balloon material.

In alternative embodiments, the treatment element 32 can act to change the properties of the internal soft tissue of the nasal airway in conjunction with an external treatment device of fixed or variable shape, to provide additional force to change the shape of the internal and/or external nasal valve. In some embodiments, an external mold element can be combined with an internal element.

Referring again to FIGS. 3 and 4B, in some embodiments, the treatment element 32 may be configured to deliver heat energy to the nasal valve. In such embodiments, the treatment element 32 may comprise any suitable heating element. For example, the treatment element 32 may comprise electrical resistance heating elements. In alternative embodiments, the heating element may comprise conduits for delivering high-temperature fluids (e.g. hot water or steam) onto the nasal tissue. In some embodiments, a high-temperature fluid heating element may comprise flow channels that place high-temperature fluids into conductive contact with nasal tissues (e.g., through a membrane wall) without injecting such fluids into the patient's nose. In further embodiments, any other suitable heating element may be provided. In further embodiments, the treatment element 32 may comprise elements for delivering energy in other forms, such as light, laser, RF, microwave, cryogenic cooling, DC current and/or ultrasound, in addition to or in place of heating elements.

U.S. Pat. No. 6,551,310 describes embodiments of endoscopic treatment devices configured to ablate tissue at a controlled depth from within a body lumen by applying radio frequency spectrum energy, non-ionizing ultraviolet radiation, warm fluid or microwave radiation. U.S. Pat. No. 6,451,013 and related applications referenced therein describe devices for ablating tissue at a targeted depth from within a body lumen. Embodiments of laser treatment elements are described, for example, in U.S. Pat. No. 4,887,605. U.S. Pat. No. 6,589,235 teaches methods and device for cartilage reshaping by radiofrequency heating. U.S. Pat. No. 7,416,550 also teaches methods and devices for controlling and monitoring shape change in tissues, such as cartilage. The devices described in these and other patents and publications available to the skilled artisan may be adapted for use in treating portions of a nasal valve or adjacent tissue as described herein. U.S. Pat. Nos. 7,416,550, 6,589,235, 6,551,310, 6,451,013 and 4,887,605 are hereby incorporated by reference in their entireties.

In alternative embodiments, similar effects can be achieved through the use of energy removal devices, such as cryogenic therapies configured to transfer heat energy out of selected tissues, thereby lowering the temperature of targeted tissues until a desired level of tissue modification is achieved. Examples of suitable cryogenic therapy delivery elements are shown and described, for example, in U.S. Pat. Nos. 6,383,181 and 5,846,235, the entirety of each of which is hereby incorporated by reference.

In some embodiments, the treatment element 32 may be configured to deliver energy (e.g. heat, RF, ultrasound, microwave) or cryotherapy uniformly over an entire outer surface of the treatment element 32, thereby treating all nasal tissues in contact with the treatment element 32. Alternatively, the treatment element 32 may be configured to deliver energy at only selective locations on the outer surface of the treatment element 32, in order to treat selected regions of nasal tissues. In such embodiments, the treatment element 32 may be configured so that energy being delivered to selected regions of the treatment element can be individually controlled. In some embodiments, portions of the treatment element 32 are inert and do not deliver energy to the tissue. In further alternative embodiments, the treatment element 32 may be configured with energy-delivery (or removal) elements distributed over an entire outer surface of the treatment element 32. The control system 42 may be configured to engage such distributed elements individually or in selected groups, to treat only targeted areas of the nasal passageway.

Figure 5:
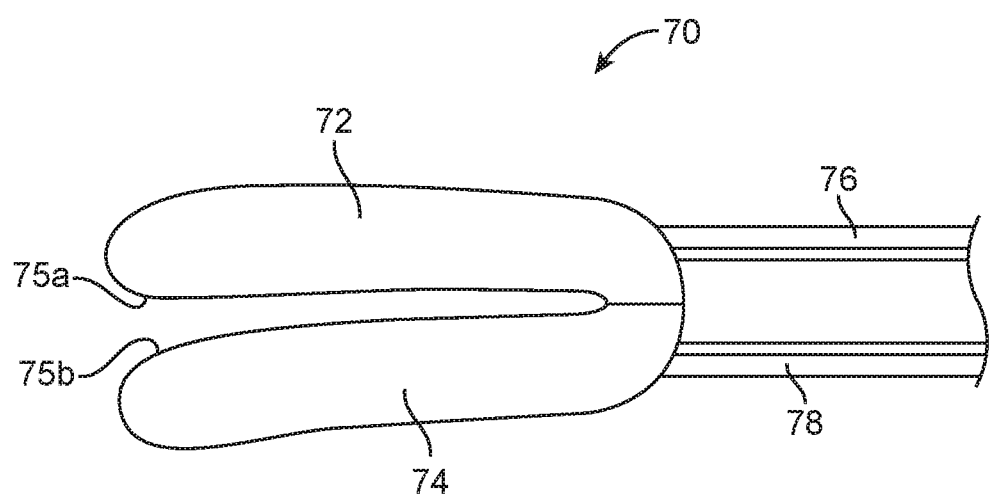
FIG. 5 is a side view of a distal portion of an upper airway treatment system, including a two-nostril, inflatable balloon treatment element, according to one embodiment.

FIG. 5 is a side view of a distal end of an upper airway treatment device 70, according to an alternative embodiment. This embodiment includes a bifurcated treatment element, made up of a pair of semi-ellipsoid elements 72, 74 sized and configured to be inserted into the two nostrils of a patient—i.e., with the two elements 72, 74 on opposite sides of the nasal septum. In various embodiments, the elements 72, 74 may be two parts of an inflatable balloon or two separate inflatable balloons. The elements 72, 74 may each have a medial surface 75a, 75b, which may be substantially flat, curved or otherwise shaped and configured to contact the nasal septum. In some embodiments, the elements 72, 74 may include expandable balloons with independent inflation lumens 76, 78. In alternative embodiments, the elements 72, 74 have substantially fixed non-expandable shapes. In still further embodiments, the elements 72, 74 may include self-expandable sections. In some embodiments, the bifurcated treatment element halves 72, 74 may also carry energy delivery members, such as those described above. In some embodiments, the shape of the elements 72, 74 may be modified by the operator to impart an optimal configuration to the treated tissue. The shape modification of elements 72, 74 can be accomplished pre-procedure or during the procedure and can be either fixed after modification or capable of continuous modification.

Figure 6:
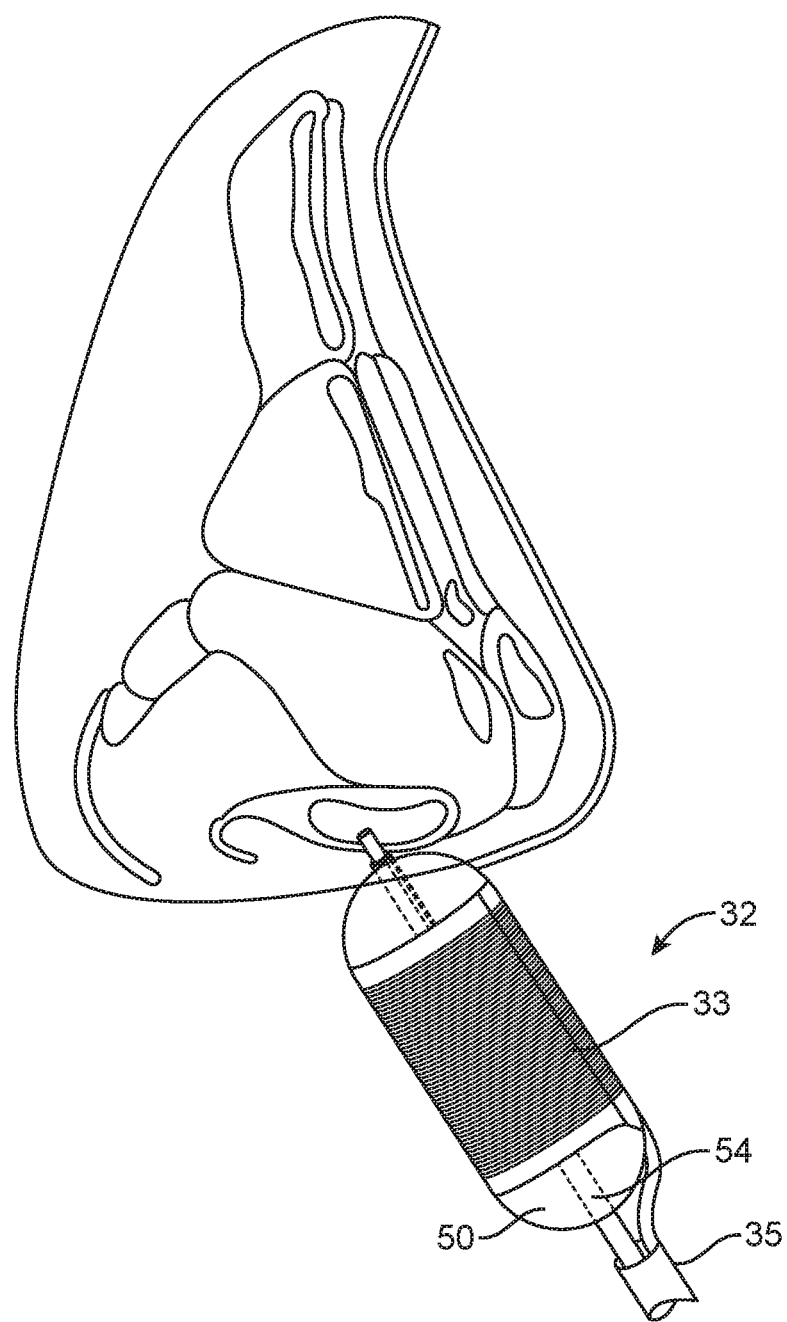
FIG. 6 is a perspective view of patient's nose and a distal portion of the upper airway treatment system of FIG. 5, illustrating the beginning of an advancement of the device into a nostril, according to one embodiment.

FIG. 6 is a stylized, perspective view of the treatment element 32 of the upper airway treatment device 30 of FIG. 3 being inserted into a patient's nostril for treatment. In this figure, for illustrative purposes, the balloon 50 is shown inflated. Although this may be one possible way to insert the balloon 50, more typically the balloon 50 will be inserted in its uninflated configuration and then inflated when in place within the nostril. Once inserted into a nostril to a desired depth, the balloon 50 is inflated, which may expand the nostril, move various structures (lateral wall, septum) and/or even break one or more bony structures, such as the nasal turbinates. When the balloon 50 is in place and inflated, energy may be delivered to mucosal and/or submucosal tissues via the energy delivery member 33. This energy delivery might help reshape the nasal airway and/or may change a property of one or more airway tissues, as previously described. The balloon 50 may be maintained in its inflated state within the nostril for as long as desired or until the treatment is thought to be complete. Energy delivery may be performed for as long as desired as well. After the treatment is complete, the balloon 50 is deflated, and the treatment element 32 is removed from the nostril. In some cases, the same treatment element 32 may be used again, for the patient's other nostril. Alternatively, the procedure may be ended after one nostril is treated. In some cases, just the treatment element 32 is disposable and made for use in only one patient. In other embodiments, the treatment element 32 and shaft 35 are disposable, and in yet other embodiments, the treatment element 32, the shaft 35 and the handle 34 are disposable.

Several embodiments may be employed for delivering energy treatment over a desired target area in the upper airway. For example, in some embodiments, a laser treatment system may treat a large surface area by scanning a desired treatment pattern over an area to be treated. In the case of microwave or ultrasound, suitably configured transducers may be positioned adjacent to a target area, and desired transducer elements may be activated under suitable depth focus and power controls to treat a desired tissue depth and region. In some embodiments, ultrasound and/or microwave treatment devices may also make use of lenses or other beam shaping of focusing devices or controls. In some embodiments, one or more electrical resistance heating elements may be positioned adjacent to a target region and activated at a desired power level for a therapeutically effective duration. In some embodiments, such heating elements may be operated in a cyclical fashion to repeatedly heat and cool a target tissue. In other embodiments, RF electrodes may be positioned adjacent to and in contact with a targeted tissue region. The RF electrodes may then be activated at some frequency and power level for a therapeutically effective duration. In some embodiments, the depth of treatment may be controlled by controlling a spacing between electrodes. In alternative embodiments, RF electrodes may include needles, which may puncture mucosal tissue to a desired depth.

In some embodiments, the treatment element 32 and control system 42 may be configured to deliver treatment energy or cryotherapy to a selected tissue depth in order to target treatment at specific tissues. For example, in some embodiments, treatments may be targeted at tightening sections of the epithelium of the inner surface of the nasal valve. In other embodiments, treatments may be targeted at strengthening soft tissues underlying the epithelium. In further embodiments, treatments may be targeted at strengthening cartilage in the area of the upper lateral cartilage. In still further embodiments, treatments may be targeted at stimulating or modifying the tissue of muscles of the nose or face in order to dilate the nasal valve.

In some embodiments, the treatment element 32 and control system 42 may be configured to deliver treatment energy to create specific localized tissue damage or ablation, stimulating the body's healing response to create desired conformational or structural changes in the nasal valve tissue. In some embodiments, the treatment element 32 and control system 42 may be configured to create specific localized tissue damage or ablation without the application of energy. For example the treatment element 32 may be configured to chemically cauterize tissue around a nasal valve by delivering a cauterizing agent (e.g., silver nitrate, trichloroacetic acid, cantharidin, etc.) to the tissue. The treatment element 32 may comprise apertures configured to permit the cauterizing agent to pass through to the nose. In some embodiments, the treatment element 32 may aerosolize the cauterizing agent. Other delivery methods are also contemplated. The treatment element 32 may comprise a lumen through which the cauterizing agent passes. The lumen may be fluidly connected to a reservoir or container holding the cauterizing agent. The device may comprise an input control (e.g., a button or switch) configured to control the delivery of the cauterizing agent. In some embodiments, the treatment element 32 comprises an applicator that can be coated in a cauterizing agent (e.g., dipped in a reservoir of cauterizing agent, swabbed with cauterizing agent, etc.) and the coated treatment element applicator may be applied to the tissue to be treated. In some embodiments, the treatment element may be configured to apply cauterizing agent to the patient over a prolonged period of time (e.g., 30 seconds, 1 minute, 2 minutes, etc.). In some embodiment, the treatment element 32 comprises shields configured to protect tissue surrounding the tissue to be treated from coming into contact with the cauterizing agent. In some embodiments, a separate element is used to shield tissue surrounding the tissue to be treated from coming into contact with the cauterizing agent. While such treatments may be performed without the application of energy, in some embodiments, they are performed in conjunction with energy treatments.

In some embodiments, a treatment element may be configured to treat a patient's nasal valve by applying energy (or removing energy, in the case of cryotherapy) from a position outside the patient's nose. For example, a device may be placed on the external surface of the nose that would pull skin to effect a change in the nasal airway. Treatment may then be applied to the internal and/or external nasal tissue to achieve a desired nasal valve function. In some embodiments, the device is configured to position tissue to be reshaped. In some embodiments, the device comprises features and mechanisms to pull, push or position the nasal tissue into a mold for reshaping. For example, suction, counter traction, or compression between two parts of the device may be used.

In some embodiments, the treatment device comprises one, two, three, four, or more molds configured to reshape tissue. The mold or reshaping element may be fixed in size or may vary in size. The mold may also be fixed in shape or may vary in shape. For example, the size or shape of the element may be varied or adjusted to better conform to a nasal valve of a patient. Adjustability may be accomplished using a variety of means, including, for example, mechanically moving the mold by way of joints, arms, guidewires, balloons, screws, stents, and scissoring arms, among other means. The mold may be adjusted manually or automatically. The mold is configured to impart a shape to the tissues of the nasal valve area to improve airflow or perceived airflow. The mold is configured to act near the apex of the nasal valve angle, the point at which the upper lateral cartilage meets the cartilage of the nasal septum. It may be desirable to treat in an area near, but not at, the nasal valve to avoid post procedure scarring and/or adhesions. This may be accomplished by focusing treatment on the lateral part of the nasal valve angle.

In some embodiments of treatment devices comprising an array or multiple pairs of electrodes, each pair of electrodes (bipolar) or each electrode (monopolar) may have a separate, controlled electrical channel to allow for different regions of the treatment element to be activated separately.

In some embodiments, the treatment system 30 may be configured to heat specific tissue while maintaining lower temperatures in other adjacent tissue. Any suitable tissue cooling devices or members may be incorporated into any embodiment of the treatment system 30 and methods described herein. The nasal valve is an example of a tissue complex that includes adjacent tissues that may benefit from being maintained at different temperatures. Other examples include the skin, which comprises the epidermis, dermis, and subcutaneous fat, the tonsils, which comprise mucosa, glandular tissue, and vessels. Treatment of other tissue complexes is also possible. For example, in some embodiments, the internal structures of the nasal valve may be heated while maintaining a lower temperature in the mucosal lining of the nose and/or skin. In other embodiments, the mucosa may be heated, while maintaining lower temperatures in the skin. Limiting unwanted heating of non-target tissues may allow trauma and pain to be reduced, may reduce scarring, may preserve tissue function, and may also decrease healing time. Combinations of heat transfer and/or heat isolation may allow directed treatment of specific tissue such as cartilage, while excluding another tissue, such as mucosa, without surgical dissection.

Generally, when using the treatment element 32 with the energy delivery member 33 (e.g., monopolar RF electrode) to heat nasal cartilage, the energy delivery member 33 will be in contact with the mucosa. When the energy delivery member 33 is activated, both the mucosa and the cartilage are heated by the current flowing from the energy delivery member 33 to the return (e.g., ground pad). The tissue closest to the energy delivery member 33 receives the highest current density, and thus, the highest heat. A surface cooling mechanism may allow the temperature of the electrode surface to be reduced. Such a cooling mechanism may maintain a lower temperature at the mucosa, even though current flow will continue to heat the cartilage.

In some embodiments, temperature of the area around the electrode during treating is from about 30 degrees C. to about 90 degrees C. In some embodiments, temperature of the area around the electrode during treating is from about 40 degrees C. to about 80 degrees C. In some embodiments, temperature of the area around the electrode during treating is from about 50 degrees C. to about 70 degrees C. In some embodiments, temperature of the area around the electrode during treating is about 60 degrees C. In some embodiments, for example during cryotherapy, temperature of the area around the electrode may be lower. In some embodiments, treating the target tissue comprises treatment for about 3 minutes. In some embodiments, treating the target tissue comprises treatment for about 10 seconds to about 2 minutes. In some embodiments, treating the target tissue comprises treatment for about 15 seconds to about 1 minute. In some embodiments, treating the target tissue comprises treatment for about 20 seconds to about 45 seconds. In some embodiments, treating the target tissue comprises treatment for about 30 seconds. In some embodiments, treating the target tissue comprises delivering between about 1 and about 100 watts to the tissue. In some embodiments, treating the target tissue comprises delivering between about 5 and about 75 watts to the tissue. In some embodiments, treating the target tissue comprises delivering between about 10 and about 50 watts to the tissue.

In one embodiment, a method of decreasing airflow resistance in a nasal valve comprises the steps of inserting an energy-delivery or cryotherapy device into a nasal passageway, and applying energy or cryotherapy to a targeted region or tissue of the nasal passageway. For example, in some embodiments, the method may include delivering energy or cryotherapy to a section of internal nasal valve cartilage in the area of the upper lateral cartilage, or in the area of intersection of the upper and lower lateral cartilage. In alternative embodiments, the method may deliver energy to the epithelium, or underlying soft tissue adjacent to the upper lateral cartilage and/or the intersection of the ULC and the LLC.

In another embodiment, a method comprises heating a section of nasal valve cartilage to be reshaped, applying a mechanical reshaping force, and then removing the heat. In some embodiments, the step of applying a mechanical reshaping force may occur before, during or after the step of applying heat.

In some embodiments, the method may further include the step of inserting a reshaping device into the nasal passageway after applying an energy or cryotherapy treatment. In such embodiments, a reshaping device such as an external adhesive nasal strip (such as those described for example in U.S. Pat. No. 5,533,499 to Johnson or U.S. Pat. No. 7,114,495 to Lockwood, the entirety of each of which is hereby incorporated by reference) may be applied to the exterior of the nose after the treatment, in order to allow for long-term reshaping of nasal valve structures as the treated tissues heal over time. In alternative embodiments, a temporary internal reshaping device (such as those taught in U.S. Pat. No. 7,055,523 to Brown or U.S. Pat. No. 6,978,781 to Jordan, the entirety of each of which is hereby incorporated by reference) may be placed in the nasal passageway after treatment in order to allow for long-term reshaping of nasal valve structures as the treated tissues heal over time. In some embodiments, the dilating nasal strips can be worn externally until healing occurs.

In alternative embodiments, internal and/or external reshaping devices may be used to reshape a nasal valve section prior to the step of applying energy or cryotherapy treatments to targeted sections of the epithelial, soft tissue, mucosa, submucosa and/or cartilage of the nose. In some embodiments, the energy or cryotherapy treatment may be configured to change the properties of treated tissues such that the tissues will retain the modified shape within a very short time of the treatment. In alternative embodiments, the treatment may be configured to reshape nasal valve structures over time as the tissue heals.

In some embodiments, a portion of the nose, the nasal valve and/or the soft tissue and cartilage of the nasal valve may be reshaped using a reshaping device and then fixed into place. In some embodiments, such fixation may be achieved by injecting a substance such as a glue, adhesive, bulking agent or a curable polymer into a region of the nasal tissue adjacent the target area. Alternatively, such a fixation substance may be applied to an external or internal surface of the nose.

In some embodiments, an injectable polymer may be injected into a region of the nose, either below the skin on the exterior of the nose, or under the epithelium of the interior of the nose. In some embodiments, an injectable polymer may include a two-part mixture configured to polymerize and solidify through a purely chemical process. One example of a suitable injectable two-part polymer material is described in U.S. Patent Application Publication No. 2010/0144996, the entirety of which is hereby incorporated by reference. In other embodiments, an injectable polymer may require application of energy in order to cure, polymerize or solidify. A reshaping device may be used to modify the shape of the nasal valve before or after or during injection of a polymer. In embodiments employing an energy-curable polymer, a reshaping device may include energy-delivery elements configured to deliver energy suitable for curing the polymer to a desired degree of rigidity.

In another embodiment, the muscles of the nose and/or face are stimulated to dilate the nasal valve area prior to or during application of other treatments such as energy/cryo application or fixation treatments. In such embodiments, the muscles to be treated may include the nasal dilator muscles (nasalis) the levetator labii, or other facial muscles affecting the internal and/or external nasal valves. In some embodiments, the targeted muscles may be stimulated by applying an electric current to contract the muscles, mentally by the patient, or manually by the clinician.

In some embodiments, the muscles of the nose and/or face may also be selectively deactivated through chemical, ablative, stimulatory, or mechanical means. For example, muscles may be deactivated by temporarily or permanently paralyzing or otherwise preventing the normal contraction of the muscle tissue. Chemical compounds for deactivating muscle tissues may include botulinum toxin (aka "botox"), or others. Ablative mechanisms for deactivating muscle tissue may include RF ablation, laser ablation or others. Mechanical means of deactivating muscle tissues may include one or more surgical incisions to sever targeted muscle tissue.

In some embodiments, energy may be applied to the skin of the nose to effect a shrinkage of the skin, epidermis, dermis, subdermal, subcutaneous, tendon, ligament, muscle, cartilage and/or cartilage tissue. The tissue shrinkage is intended to result in a change of forces acting on the tissues of the nasal valve to improve airflow through the nasal airway.

In another embodiment, the nasal valve tissue may be damaged or stimulated by energy application, incisions, injections, compression, or other mechanical or chemical actions. Following such damage, a device may be used on the tissue to mold or shape the tissue of the valve during healing. In some embodiments, such a reshaping device may be temporarily placed or implanted inside or outside the patient's nose to hold a desired shape while the patient's healing process progresses.

In another embodiment, the aesthetic appearance of the nose may be adjusted by varying the device design and/or treatment procedure. The predicted post-procedure appearance of the nose may be shown to the patient through manipulating the nasal tissue to give a post procedure appearance approximation. The patient may then decide if the predicted post procedure appearance of the face and nose is acceptable or if the physician needs to change parameters of the device or procedure to produce an appearance more acceptable to the patient.

In another embodiment, reduction of the negative pressure in the nasal airway can be effected to reduce collapse of the structures of the nasal airway on inspiration without changing a shape of the nasal valve. For example, this may be accomplished by creating an air passage that allows flow of air directly into the site of negative pressure. One example of this is creating a hole through the lateral wall of the nose allowing airflow from the exterior of the nose through the nasal wall and into the nasal airway.

In another embodiment, energy, mechanical or chemical therapy may be applied to the tissue of the nasal airway with the express purpose of changing the properties of the extracellular matrix components to achieve a desired effect without damaging the chondrocytes or other cells of the nasal airway tissue.

The method may include identifying a patient who desires to improve the airflow through their nasal passageways and/or who may benefit from an increase in a cross-sectional area of the opening of the nasal valve. The patient may be positioned either in an upright position (e.g., seated or standing) or be lying down. Local anesthesia may be applied to an area near or surrounding the tissue to be treated. General anesthesia may also be used.

Optionally, a positioning element, like that described herein, may be used to measure a desired depth or angle of treatment. As described above, the positioning element may be inserted to the desired depth of treatment and rotated to a desired angle of treatment. Marks along the positioning element can indicate the desired depth. Marks along the base of the shaft of the positioning element can indicate the desired angle. The physician or other medical professional administering the treatment can then insert the treatment device to the desired location. The physician may also assess any other characteristics relevant to the treatment of the patient's nose that may influence the manner of treatment. In some embodiments, a reshaping element may be used to manipulate the nasal tissue into a configuration allowing improved airflow; and treatment may be performed while such a reshaping element is maintaining the desired configuration of the nasal tissue.

If the treatment device comprises a monopolar electrode or electrode needles, a ground pad may be attached to the patient. The ground pad may be attached at the patient's torso, for example the shoulder or abdomen. Other locations are also possible, such as the patient's buttocks. Preferably, the point of attachment is a large, fleshy area. After being attached, the ground pad may be plugged into a power source. If the device is powered by a remote generator (e.g., RF generator), the device may then be plugged into the generator.

Figure 7A:
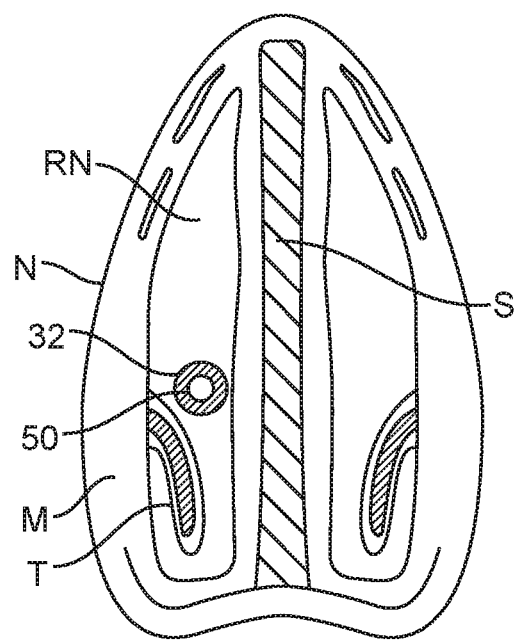
FIGS. 7A and 7B are front, cross-sectional views of a human nose, illustrating a procedure for treating the nose with an inflatable balloon treatment element, according to one embodiment.
Figure 7B:
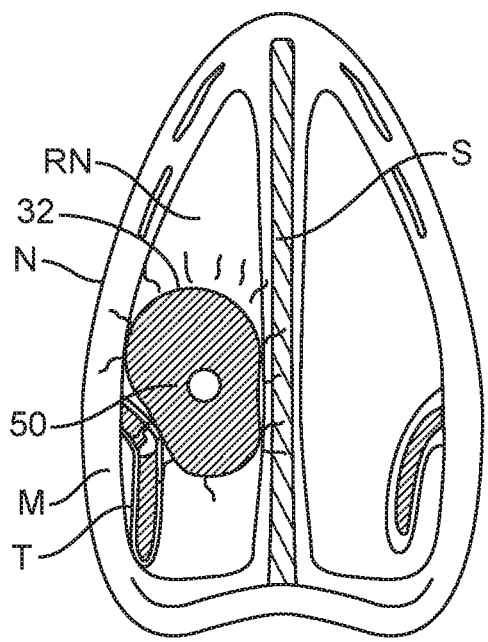

Referring now to FIGS. 7A and 7B, a simplistic version of a method for treating a nasal airway with the treatment element 32 of the treatment system 30 is illustrated. As with previously described embodiments, the treatment element 32 includes an inflatable balloon 50. In FIG. 7A, the treatment element 32 has been advanced into the right nostril RN of the patient's nose N, to the right of the nasal septum S, with the balloon 50 in its uninflated state. The treatment element 32 is shown here in frontal cross-section, but it could also be positioned in the right nostril RN in a different orientation, for example more top-to-bottom than is shown here. Thus, the method is not limited to any certain orientation of the treatment element 32 in the nostril RN. As shown, the treatment element 32 is located near one of the nasal turbinates T, between the surface of the nasal mucosa M of the lateral wall and the nasal septum S. In FIG. 7A, the mucosa M is somewhat swollen.

In FIG. 7B, the balloon 50 has been inflated and is now pressing against the nasal turbinate T, the nasal septum S, and the mucosa M. In an actual nostril, there are multiple turbinates T, but only one is shown here, for clarity of illustration. The inflatable balloon 50 is strong enough, and has been inflated with sufficient pressure, to break the thin bone of the turbinate T and move it to the side, closer to the nasal wall. This broken bone will likely heal in this new configuration, thus potentially decreasing airflow resistance in the right nostril RN. Additionally, the mucosa M has been pushed down by the balloon 50, thus reducing swelling, and at least some of this shape change may remain after the treatment. In some cases, energy may be delivered (small, squiggly lines) from the balloon 50 while it is in its inflated state. The energy may be RF energy or any other form of energy, as described above, and it may help the nostril RN to retain at least some of the shape changes conferred by the balloon 50 during the treatment. As described above, one way to deliver energy is to inflate the balloon 50 with heated or cooled inflation fluid.

After the treatment is performed, the balloon 50 is deflated, and the treatment element 32 is removed from the nostril RN. Typically, the shape changes made to the structures that make up the nostril RN will be at least partially retained, after the procedure is completed and the patient's nose has time to heal. In alternative embodiments of this method, additional structures or different structures may be addressed. For example, the nasal septum may be moved to one side, for example in the case of a deviated septum. Alternatively, cartilage of the lateral wall may be moved out laterally, to expand the diameter of the nasal valve, or any combination of these changes could be made. Any of these embodiments may involve moving soft tissue or bone, and in some cases, as here, bone may be broken and moved.

Figure 8A:
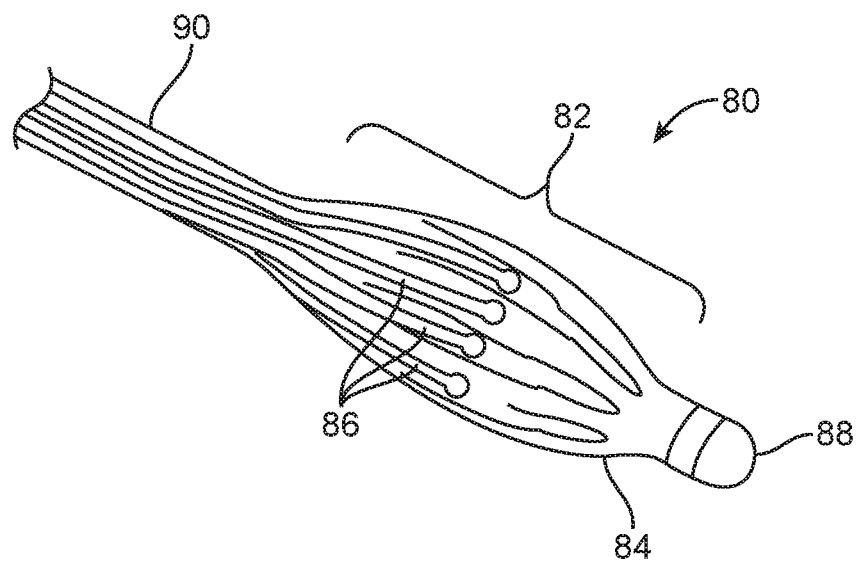
FIGS. 8A and 8B are perspective views of a distal portion of an airway treatment device including an inflatable balloon and expandable RF energy delivery electrodes, according to one embodiment.
Figure 8B:
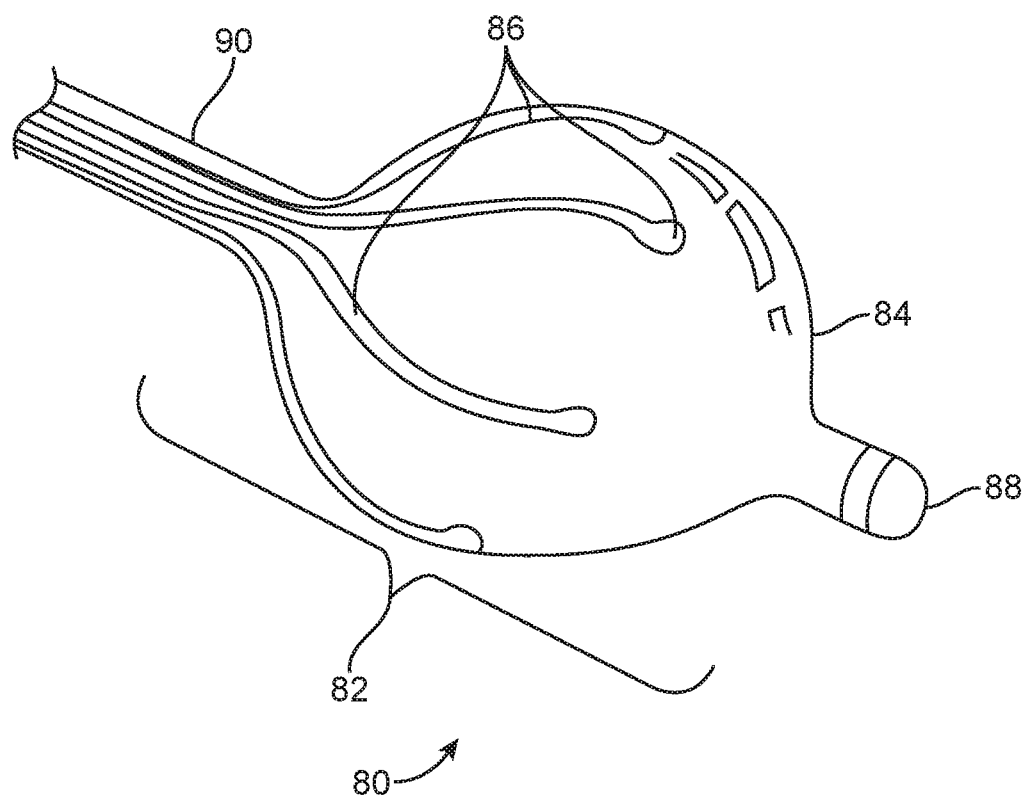

Referring now to FIGS. 8A and 8B, a distal portion of another embodiment of an upper airway treatment device 80 is illustrated. This device 80 may be used with or incorporated into any treatment system or method described above. In this embodiment, the distal end of the treatment device 80 includes a treatment element 82 coupled with a shaft 90 at is proximal end and an atraumatic distal tip 88. The treatment element 82 includes an inflatable balloon 84, as described above, and multiple longitudinal, expandable RF electrodes 86 disposed about the circumference of the balloon 84. The electrodes 86 may be made out of any suitable conductive metal, as described above. FIG. 8A illustrates the treatment element in the uninflated, insertion configuration. FIG. 8B illustrates the treatment element in the inflated, treatment configuration. The electrodes 86 may be either bipolar or monopolar, according to various alternative embodiments.

Although this is believed to be a complete and accurate description of embodiments, the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A method for reshaping a nasal airway in a patient, without forming an incision or leaving behind an implant, the method comprising:
    advancing an inflatable balloon of a reshaping device in an uninflated configuration into a nostril of the patient and between a nasal septum and a lateral wall of the nasal airway;
    inflating the inflatable balloon with sufficient pressure to cause the inflatable balloon to press against the lateral wall to increase a nasal valve angle and thus increase a diameter of the nasal airway; and
    removing the reshaping device from the nasal airway, wherein the diameter of the nasal airway remains increased after removal of the reshaping device and healing of the nasal airway.

2. The method of claim 1, wherein the inflatable balloon is positioned between an upper portion of the nasal septum and the lateral wall, wherein the inflatable balloon is inflated until the nasal valve angle reaches a desired size, and wherein the diameter of the nasal airway comprises a diameter at or near a nasal valve of the nasal airway.

3. The method of claim 1, further comprising delivering energy with at least one energy delivery member coupled with the inflatable balloon to an underlying tissue beneath nasal mucosa of the nasal airway, while maintaining the balloon in an inflated configuration.

4. The method of claim 3, wherein the at least one energy delivery member comprises at least one radiofrequency member attached to an outer surface of the inflatable balloon, and wherein delivering the energy comprises delivering radiofrequency energy to heat the underlying tissue.

5. The method of claim 4, wherein the at least one radiofrequency member comprises multiple flexible electrodes that flex outward when the inflatable balloon is inflated.

6. The method of claim 3, wherein delivering the energy comprises delivering a form of energy selected from the group consisting of radiofrequency, ultrasound, microwave, heat, electrical, light and laser energy.

* * * * *